United States Patent [19]

Tone et al.

[11] Patent Number: 5,607,934
[45] Date of Patent: Mar. 4, 1997

[54] PIPERAZINE DERIVATIVES AND SALTS THEREOF

[75] Inventors: Hitoshi Tone, Itano; Masatoshi Morisue, Naruto; Katsumi Tamura, Itano; Toshiki Miyazaki, Tokushima; Yoshimasa Nakano, Itano, all of Japan

[73] Assignee: Otsuka Pharmaceutical Co., Ltd., Tokyo, Japan

[21] Appl. No.: 397,043

[22] PCT Filed: Jul. 1, 1994

[86] PCT No.: PCT/JP94/01071

§ 371 Date: Mar. 10, 1995

§ 102(e) Date: Mar. 10, 1995

[87] PCT Pub. No.: WO95/02593

PCT Pub. Date: Jan. 26, 1995

[30] Foreign Application Priority Data

Jul. 13, 1993 [JP] Japan .................................. 5-172780

[51] Int. Cl.$^6$ ..................... A61K 31/495; C07D 241/02; C07D 403/02; C07D 241/04
[52] U.S. Cl. .................. 514/253; 514/252; 514/255; 544/357; 544/368; 544/370; 544/385
[58] Field of Search .................. 544/357, 368, 544/370, 385; 514/252, 253, 255

[56] References Cited

PUBLICATIONS

Synthesis of 2,5-dioxygenated pyrazine 4-oxides: total synthesis of a new inhibitor of superoxide anion generation, OPC-15161, Yasuyuki Kita et al., J. of the Chemical Society, Perkin Transactions 1, No. 7, Apr. 1994, pp. 875-884.
Pyrazine Chemistry, A. Kayhan Gokturk et al., Chem. Abstr., vol. 97, (1982) 38916u.
Stereochemical studies on the biosynthesis of the αβ-didehydro amino acid units of mycelianamide, cyclopenin, and cyclopenol, Gordon W. Kirby et al., Chem. Abstr., vol. 85, (1976) 173991g.
Isolation of some new 3,6-dialkyl-1,4-dihydroxy-piperazine-2,5-diones from Aspergillus terreus, Mary J. Garson et al., Chem. Abstr., vol. 105, (1986) 111582x.
Conversion of N-hydroxytryptophans into .alpha.,.beta.-dehydrotryptophan, Ralf Plate et al., Chem. Abstr., vol. 108 (1987) 222064m.
Conversion of N-hydroxytryptophan into .alpha.-functionalized tryptophans, Ralf Plate et al., Chem. Abstr., vol. 109 (1987) 23333u.
N-Hydroxy amides. Part 6. Synthesis and spectroscopic properties of 1-hydroxypiperazine-2,5-diones, Masayasu Akiyama et al., Chem. Abstr., vol. 111 (1989) 134729p.
Pulcherrimin: A synthesis of 1,4-dihydroxy-2,5-dioxopiperazines A. H. Cook et al., Chem. Abstr., vol. 51 (1957) 8763c.
Studies in relation to biosynthesis. XXIX. Terpenoid chain of mycelianamide, A. J. Birch et al., Chem. Abstr., vol. 57 (1962) 5958.

Biosynthetic incorporation of stereoselectively labeled tyrosine–βH into mycelianamide, Gordon W. Kirby et al., Chem. Abstr., vol. 79 (1973) 15643s.
Total synthesis of (±)-mycelianamide, Noboru Shinmon et al., Chem. Abstr., vol. 94 (1981) 121466f.
α–Functionalized amino acid derivatives. A synthetic approach of possible biogenetic importance, Jacobus D. M. Herscheid, Chem. Abstr., vol. 93 (1980) 8480x.
Biosynthesis of gliotoxin. Synthesis of sulfur–bridged dioxopiperazines from N–hydroxyamino acids, Jacobus D. M. Herscheid et al., Chem. Abstr., vol. 93 (1980) 26386a.
1,4–Dihydroxy–2,5–dioxopiperazines from activated N–hydroxyamino acids, Jacobus D. M. Herscheid et al., Chem. Abstr., vol. 95 (1981) 97729s.
N–Hydroxytryptophan in the synthesis of natural products containing oxidized dioxopiperazines. An approach to the neoechinulin and sporidesmin series, Harry C. J. Ottenheijm et al., Chem. Abstr., vol.97 (1982) 6749a.
Synthesis and reaction of αβ–unsaturated α–nitro carboxylic esters, Chung Ch'i Shin et al., Chem. Abstr., vol. 74 (1971) 12570b.
The αβ–unsaturated carboxylic acid derivatives. IX. Cyclization of α(N–acylhydroxyamino)acid esters with ammonia or hydroxylamine, Chung–Gi Shin et al., Chem. Abstr., vol. 84 (1976) 17694m.
αβ–Unsaturated carboxylic acid derivatives. XIII. The synthesis and configuration of alkyl 2–acyl–amino–2–alkenoates and their cyclized 2,5–piperazinedione derivatives, Chung–Gi Shin, Chem. Abstr., vol. 88 (1978) 190747m.
Standardized one–and two–dimensional thin–layer chromatographic methods for the identification of secondary metabolites in Penicillium and other fungi, R. R. M. Paterson, Chem. Abstr., vol. 106 (1986), 29448v.

(List continued on next page.)

Primary Examiner—Cecilia Tsang
Attorney, Agent, or Firm—Finnegan, Henderson, Farabow, Garrett & Dunner

[57] ABSTRACT

Piperazine compounds and salts thereof having inhibitory effect against superoxide radicals ($O_2^-$). The piperazine compounds have the general formula:

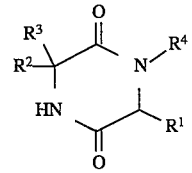

wherein
$R^1$ is a lower alkyl group;
$R^2$ is a phenyl-lower alkyl group which may have 1 to 3 substituents, on the phenyl ring, selected from the group consisting of a hydroxyl group, a phenyl-lower alkoxy group, a lower alkyl group, a lower alkoxy group and a halogen atom;
$R^3$ is a hydrogen atom, a lower alkyl group or a phenyl-lower alkyl group; and
$R^4$ is a hydroxyl group, a phenyl-lower alkoxy group or a tetrahydropyranyloxy group.

30 Claims, No Drawings

OTHER PUBLICATIONS

High–performance liquid chromatographic determination of profiles of mycotoxins and other secondary metabolites, Jens C. Frisvad, Chem. Abstr., vol. 107 (1987) 36247c.

Standardized high–performance liquid chromatography of 182 mycotoxins and other fungal metabolites based on alkylphenone retention indexes and UV–VIS spectra (diode array detection), Jens Frisvad et al., Chem. Abstr., vol. 107 (1987) 192376z.

Gradient high–performance liquid chromatography using alkylphenone retention indices of insecticidal extracts of Penicillium strains, R. Russell et al., Chem. Abstr., vol. 112 (1989) 115080z.

Neutral, alkaline and difference ultraviolet spectra of secondary metabolites from Penicillium and other fungi, and comparisons to published maxima from gradient high–performance liquid chromatography with diodearray detection, R. Russell et al., Chem. Abstr., vol. 113 (1990) 128844x.

Structure of cyclo(–N–hydroxyglycyl–L–phenylalanyl–), Yoshinobu Yokomori et al., Chem. Abstr., vol. 112 (1990) 227120u.

Structure of cyclo(–N–hydroxyglycyl–L–alanyl–), Yoshinobu Yokomori et al., Chem. Abstr., vol. 111 (1990) 144490t.

The $C_{10}OH_{17}$ side chain in mycelianamide. Stereochemistry of bergamottin and unbelliprenin, R. B. Bates et al., Chem. Abstr., vol. 60 (1964) 5557.

Etzionin, a new antifungal metabolite from a Red Sea tunicate, Shulamit Hirsch et al., Chem. Abstr., vol. 111 (1989) 229294g.

Preparation and properties of crystalline candidin, L. C. Vining et al., Chem. Abstr., vol. 51 (1957) 3618.

Biosynthesis of gliotoxin and mycelianamide, J. C. MacDonald et al., Chem. Abstr., vol. 82 (1975) 167344v.

Origin of the terpenoid structures in mycelianamide and mycophenolic acid, A. J. Birch et al., Chem. Abstr., vol. 52 (1958) 3023.

PIPERAZINE DERIVATIVES AND SALTS THEREOF

This application is a 371 of PCT/JP94/01071, filed Jul. 1, 1994.

FIELD OF THE INDUSTRIAL UTILIZATION

The present invention relates to novel piperazine derivatives and salts thereof.

BACKGROUND ART

There have been known some piperazine derivatives having chemical structural formulae similar to those of the piperazine derivatives of the present invention, from the following prior art references, i.e. EP-A2-303250 and U.S. Pat. No. 5,021,419.

DISCLOSURE OF THE INVENTION

The present invention provides piperazine derivatives and salts thereof, which are novel and are not known in prior art references. Said piperazine derivatives are represented by the following general formulae (1) and (2):

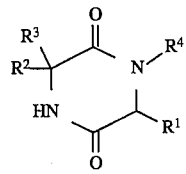
(1)

wherein $R^1$ is a lower alkyl group;

$R^2$ is a phenyl-lower alkyl group which may have, on the phenyl ring, 1 to 3 substituents selected from the group consisting of a hydroxyl group, a phenyl-lower alkoxy group, a lower alkyl group, a lower alkoxy group and a halogen atom, an imidazolyl-substituted lower alkyl group which may have phenyl-lower alkyl group(s) as the substituent(s) on the imidazolyl ring, or a group of the formula:

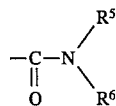

(wherein $R^5$ and $R^6$ are the same or different and are each a hydrogen atom, a benzothiazolyl group, or a phenyl-lower alkyl group which may have, on the phenyl ring, 1 to 3 substituents selected from the group consisting of a lower alkoxy group, a phenyl-lower alkoxy group, a lower alkyl group and a hydroxyl group; further, said $R^5$ and $R^6$ and the adjacent nitrogen atom bonding thereto may form, together with or without other nitrogen atom or an oxygen atom, a 5- to 6-membered saturated heterocyclic group; said heterocyclic group may have, as the substituent(s), phenyl group(s) which may have lower alkoxy group(s) as the substituent(s) on the phenyl ring);

$R^3$ is a hydrogen atom, a lower alkyl group or a phenyl-lower alkyl group; and $R^4$ is a hydroxyl group, a phenyl-lower alkoxy group or a tetrahydropyranyloxy group; and

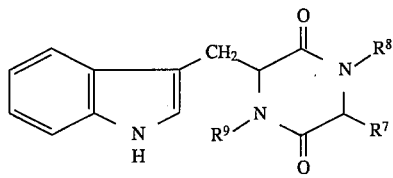
(2)

wherein $R^7$ is a lower alkyl group, a phenyl-lower alkyl group which may have, on the phenyl ring, substituent(s) selected from the group consisting of a hydroxyl group and a phenyl-lower alkoxy group, a lower alkylthio group-substituted lower alkyl group, a phenyl-lower alkoxy group-substituted lower alkyl group, a lower alkoxycarbonyl group, a lower alkoxycarbonyl group-substituted lower alkyl group or a hydroxyl group-substituted lower alkyl group;

$R^8$ is a hydrogen atom; further $R^7$ and $R^8$ may form a trimethylene group together; and $R^9$ is a hydroxyl group or a phenyl-lower alkoxy group.

The piperazine derivatives represented by the above general formulae (1) and (2) and the salts thereof according to the present invention possess an inhibitory effect against superoxide radical ($O_2^-$) released from the macrophage cells of guinea pig by stimulation, and also possess an anti-albuminuria activity in Masugi nephritis. Thus, the piperazine derivatives represented by general formulae (1) and (2) and the salts thereof are useful agents for preventing and treating various diseases caused by the above-mentioned superoxide radical, for example, diseases of autoimmunity (e.g. rheumatoid arthritis), artheriosclerosis, ischemic heart disease, transient cerebral ischematic attack, hepatic insufficiency and renal insufficiency. They are also useful agents for preventing and treating the nephritis in various clinical fields.

In addition to the above, the piperazine derivatives of general formulae (1) and (2) and the salts thereof also possess an inhibitory effect against the proliferation of Mesangium cells which are closely related to the development of the nephritis; thus, they are useful agents for preventing and treating the proliferative nephritis.

DETAILED DESCRIPTION OF THE PREFERRED EMBODIMENTS

In the present specification, each of the substituents in general formulae (1) and (2) is specifically as follows.

The lower alkoxy group can be exemplified by straight-chain or branched-chain alkoxy groups having 1 to 6 carbon atoms, such as methoxy, ethoxy, propoxy, isopropoxy, butoxy, tert-butoxy, pentyloxy and hexyloxy groups and the like.

The lower alkyl group can be exemplified by straight-chain or branched-chain alkyl groups having 1 to 6 carbon atoms, such as methyl, ethyl, propyl, isopropyl, butyl, tert-butyl, pentyl and hexyl groups and the like.

The phenyl-lower alkyl group which may have, on the phenyl ring, 1 to 3 substituents selected from the group consisting of a hydroxyl group, a phenyl-lower alkoxy group, a lower alkyl group, a lower alkoxy group and a halogen atom, can be exemplified by phenylalkyl groups in which the alkyl moiety is a straight-chain or branched chain alkyl group having 1 to 6 carbon atoms and which may have, on the phenyl ring, 1 to 3 substituents selected from the group consisting of a hydroxyl group, a phenylalkoxy group in which the alkoxy moiety is a straight-chain or branched-chain alkoxy group having 1 to 6 carbon atoms, a straight-chain or branched-chain alkyl group having 1 to 6 carbon atoms, a straight-chain or branched-chain alkoxy group having 1 to 6 carbon atoms and a halogen atom, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-(3-methoxyphenyl)ethyl, 1-(4-methoxyphenyl)ethyl, 2-methoxybenzyl, 3-(2-ethoxyphenyl)propyl, 4-(3ethoxyphenyl)butyl, 1,1-dimethyl-2-(4-ethoxyphenyl)ethyl, 5-(4-isopropoxyphenyl)pentyl, 6-(4-hexyloxyphenyl)hexyl, 3,4-dimethoxybenzyl, 3,4,5-trimethoxybenzyl, 2,4-dimethoxybenzyl, 2,5-dimethoxybenzyl, 1-phenyl-1-hydroxymethyl, 2-hydroxy-2-phenylethyl, 3-hydroxy-3-phenylpropyl, 4-hydroxy-4-phenylbutyl, 1,1-dimethyl-2-hydroxy-2-phenylethyl, 5-hydroxy-5-phenylpentyl, 6-phenyl-6-hydroxyhexyl, 2-methyl-3-phenyl-3-hydroxypropyl, 2-(4-methoxyphenyl)-2-hydroxyethyl, 2-(3-ethoxyphenyl)-2-hydroxyethyl, 4-hydroxy-4-(3,4-dimethoxyphenyl)butyl, 3-methoxybenzyl, 4-methoxybenzyl, 2,4-diethoxybenzyl, 2,3-dimethoxybenzyl, 2,4-dimethoxybenzyl, 2,6-dimethoxybenzyl, 4-benzyloxybenzyl, 2-(3-benzyloxyphenyl)ethyl, 1-(2-benzyloxyphenyl)ethyl, 3-[2-(2-phenylethoxy)phenyl]propyl, 4-[3-(3-phenylpropoxy)phenyl]butyl, 1,1-dimethyl-2-[4-(4-phenylbutoxy)phenyl]ethyl, 5-[2-(5-phenylpentyloxy)phenyl]pentyl, 6-[3-(6-phenylhexyloxy)phenyl]hexyl, 2-hydroxybenzyl, 4-hydroxybenzyl, 2-(3-hydroxyphenyl)ethyl, 1- (4-hydroxyphenyl) ethyl, 3-(2-hydroxyphenyl)propyl, 4- (3-hydroxyphenyl) butyl, 5-(2-hydroxyphenyl)pentyl, 6- (3-hydroxyphenyl) hexyl, 3,4-dihydroxybenzyl, 3,4,5-trihydroxybenzyl, 3,5-dimethoxy-4-benzyloxybenzyl, 3,5-dimethoxy-4-hydroxybenzyl, 3,5-di-tert-butoxy-4-benzyloxybenzyl, 3,5-di-tert-butoxy-4-hydroxybenzyl, 2-methylbenzyl, 2-(3-methylphenyl)ethyl, 1-(4-methylphenyl)ethyl, 3-(2-ethylphenyl)propyl, 4-(3ethylphenyl)butyl, 1,1-dimethyl-2-(4-ethylphenyl)ethyl, 5-(4-isopropylphenyl)pentyl, 6-(4-hexylphenyl)hexyl, 3,4-dimethylbenzyl, 3,4,5-trimethylbenzyl, 2,5-dimethylbenzyl, 2-chlorobenzyl, 2-(3-chlorophenyl)ethyl, 2-fluorobenzyl, 1-(4-chlorophenyl)ethyl, 3-(2-fluorophenyl)propyl, 4-(3-fluorophenyl)butyl, 5-(4-fluorophenyl)pentyl, 1,1-dimethyl-2-(2-bromophenyl)ethyl, 6-(3-bromophenyl)hexyl, 4-bromobenzyl, 2-(2-iodophenyl)ethyl, 1-(3-iodophenyl)ethyl, 3-(4-iodophenyl)propyl, 3,4-dichlorobenzyl, 3,5-dichlorobenzyl, 2,6-dichlorobenzyl, 2,3-dichlorobenzyl, 2,4-dichlorobenzyl, 3,4-difluorobenzyl, 3,5-dibromobenzyl, 3,4,5-trichlorobenzyl, 3,5-dichloro-4-hydroxybenzyl, 3,5-dimethyl-4-hydroxybenzyl and 2-methoxy-3-chlorobenzyl groups and the like.

The lower alkoxycarbonyl group can be exemplified by straight-chain or branched-chain alkoxycarbonyl groups having 1 to 6 carbon atoms, such as methoxycarbonyl, ethoxycarbonyl, propoxycarbonyl, isopropoxycarbonyl, butoxycarbonyl, tert-butoxycarbonyl, pentyloxycarbonyl and hexyloxycarbonyl groups and the like.

The phenyl-lower alkoxy group can be exemplified by phenylalkoxy groups in which the alkoxy moiety is a straight-chain or branched-chain alkoxy group having 1 to 6 carbon atoms, such as benzyloxy, 2-phenylethoxy, 1-phenylethoxy, 3-phenylpropoxy, 4-phenylbutoxy, 1,1-dimethyl-2-phenylethoxy, 5-phenylpentyloxy, 6-phenylhexyloxy and 2-methyl-3-phenylpropoxy groups and the like.

As the halogen atom, there can be cited, for example, a fluorine atom, a chlorine atom, a bromine atom and an iodine atom.

The phenyl-lower alkyl group can be exemplified by phenylalkyl groups in which the alkyl moiety is a straight-chain or branched-chain alkyl group of 1 to 6 carbon atoms, such as benzyl, 2-phenylethyl, 1-phenylethyl, 3-phenylpropyl, 4-phenylbutyl, 1,1-dimethyl- 2-phenylethyl, 5-phenylpentyl, 6-phenylhexyl and 2-methyl-3-phenylpropyl groups and the like.

The imidazolyl-substituted lower alkyl group which may have phenyl-lower alkyl group(s) as the substituent(s) on the imidazolyl ring, can be exemplified by imidazolyl-substituted lower alkyl groups in which the lower alkyl moiety is a straight-chain or branched-chain alkyl group of 1 to 6 carbon atoms and which may have, as the substituent(s) on the imidazolyl ring, phenylalkyl group(s) whose alkyl moiety is a straight-chain or branched-chain alkyl group having 1 to 6 carbon atoms, such as (4-imidazolyl)methyl, 2-(2-imidazolyl)ethyl, 1-(4-imidazolyl)ethyl, 3-(5-imidazolyl)propyl, 4-(2-imidazolyl)butyl, 1,1-dimethyl-2-(4-imidazolyl)ethyl, 5-(5-imidazolyl)pentyl, 6-(2imidazolyl)hexyl, 2-methyl-3-(4-imidazolyl)propyl, (1-benzyl-4-imidazolyl) methyl, 2-[1-(2-phenylethyl)-4imidazolyl]ethyl, 1-[5-(1-phenylethyl)-2-imidazolyl]ethyl, 3-[1-(3-phenylpropyl)-5-imidazolyl]propyl, 4-[4(4-phenylbutyl)-2-imidazolyl]butyl, 5-[2-(5-phenyl- pentyl)-4-imidazolyl]pentyl and 6-[1-(6-phenylhexyl)-4imidazolyl]hexyl groups and the like.

The phenyl-lower alkyl group which may have, on the phenyl ring, 1 to 3 substituents selected from the group consisting of a lower alkoxy group, a phenyl-lower alkoxy group, a lower alkyl group and a hydroxyl group, can be exemplified by phenylalkyl groups in which the alkyl moiety is a straight-chain or branched-chain alkyl group of 1 to 6 carbon atoms and which may have, on the phenyl ring, 1 to 3 substituents selected from the group consisting of a straight-chain or branched-chain alkoxy group of 1 to 6 carbon atoms, a phenylalkoxy group in which the alkoxy moiety is a straight-chain or branched-chain alkoxy group of 1 to 6 carbon atoms, a straight-chain or branched-chain alkyl group of 1 to 6 carbon atoms and a hydroxyl group, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-methoxybenzyl, 3-methoxybenzyl, 4-methoxybenzyl, 2-(3-methoxyphenyl)ethyl, 1-(4-methoxyphenyl)ethyl, 2-methoxybenzyl, 3-(2-ethoxyphenyl)propyl, 4-(3-ethoxyphenyl)butyl, 1,1-dimethyl-2-(4-ethoxyphenyl)ethyl, 5-(4-isopropoxyphenyl)pentyl, 6-(4-hexyloxyphenyl)hexyl, 3,4-dimethoxybenzyl, 3,4,5-trimethoxybenzyl, 2,5-dimethoxybenzyl, 2,4-diethoxybenzyl, 2,3-dimethoxybenzyl, 2,4-dimethoxybenzyl, 2,6-dimethoxybenzyl, 4-benzyloxybenzyl, 2-(3-benzyloxyphenyl)ethyl, 1-(2-benzyloxyphenyl)ethyl, 3-[2-(2-phenylethoxy)phenyl]propyl, 4-[3-(3-phenylpropoxy)phenyl] butyl, 1,1-dimethyl-2-[4-(4-phenylbutoxy)phenyl]ethyl, 5-[2-(5-phenylpentyloxy)phenyl]pentyl, 6-[3-(6-phenylhexyloxy)phenyl]hexyl, 2-hydroxybenzyl, 2-(3-hydroxyphenyl)ethyl, 1-(4-hydroxyphenyl)ethyl, 3-(2-hydroxyphenyl)propyl, 4-(3-hydroxyphenyl)butyl, 5-(2-hydroxyphenyl)pentyl, 6-(3-hydroxyphenyl)hexyl, 3,4-dihydroxybenzyl, 3,4,5-trihydroxybenzyl, 3,5-dimethoxy-4-benzyloxybenzyl, 3,5-dimethoxy-4-hydroxybenzyl, 3,5-di-tert-butoxy-4-hydroxybenzyl, 2-methylbenzyl, 2-(3-methylphenyl)ethyl, 1-(4-methylphenyl)ethyl, 3-(2-ethylphenyl)propyl, 4-(3-ethylphenyl)butyl, 1,1-dimethyl-2-(4-ethylphenyl)ethyl, 5-(4-isopropylphenyl)pentyl, 6-(4-hexylphenyl)hexyl, 3,4-dimethylbenzyl, 3,4,5-trimethylbenzyl, 3,5-di-tert-butyl-4-hydroxybenzyl and 3,5-di-tert-butyl-4-benzyloxybenzyl groups and the like.

The 5- or 6-membered saturated heterocyclic group formed by $R^5$, $R^6$ and the adjacent nitrogen atom bonding thereto, together with or without other nitrogen atom or an oxygen atom, can be exemplified by piperazinyl, pyrrolidinyl, morpholinyl and piperidinyl groups and the like.

The above heterocyclic group which has, as the substituent(s), phenyl group(s) which may have lower alkoxy group(s) as the substituent(s) on the phenyl ring, can be exemplified by the above heterocyclic groups which have, as the substituent(s), phenyl group(s) which may have 1 to 3 straight-chain or branched-chain alkoxy groups of 1 to 6 carbon atoms as the substituent(s) on the phenyl ring, such as 4-(2-methoxyphenyl)piperazinyl, 4-(2,4-dimethoxyphenyl)piperidinyl, 3-(2,3,4-trimethoxyphenyl)morpholinyl, 2-(3-methoxyphenyl)pyrrolidinyl, 2-phenylpiperidinyl, 2-(2-ethoxyphenyl)piperazinyl, 3-(3-propoxyphenyl)piperidinyl, 2-(4-butoxyphenyl)morpholino, 3-(2-pentyloxyphenyl)pyrrolidinyl and 3-(4-hexyloxyphenyl)piperazinyl groups and the like.

The phenyl group which may have lower alkoxy group(s) as the substituent(s) on the phenyl ring, can be exemplified by phenyl groups which may have, as the substituent(s) on the phenyl ring, 1 to 3 straight-chain or branched-chain alkoxy groups of 1 to 6 carbon atoms, such as phenyl, 2-methoxyphenyl, 3-methoxyphenyl, 4-methoxyphenyl, 2-ethoxyphenyl, 3-ethoxyphenyl, 4-ethoxyphenyl, 3-isopropoxyphenyl, 4-hexyloxyphenyl, 3,4-dimethoxyphenyl, 2,5-dimethoxyphenyl and 3,4,5-trimethoxyphenyl groups and the like.

The phenyl-lower alkyl group which may have, on the phenyl ring, substituent(s) selected from the group consisting of a hydroxyl group and a phenyl-lower alkoxy group, can be exemplified by phenylalkyl groups in which the alkyl moiety is a straight-chain or branched-chain alkyl group of 1 to 6 carbon atoms and which may have, on the phenyl ring, 1 to 3 substituents selected from the group consisting of a hydroxyl group and a phenylalkoxy group whose alkoxy moiety is a straight-chain or branched-chain alkoxy group of 1 to 6 carbon atoms, such as 2-hydroxybenzyl, 3-hydroxybenzyl, 4-hydroxybenzyl, 2-(3-hydroxyphenyl)ethyl, 1-(4-hydroxyphenyl)ethyl, 3-(2-hydroxyphenyl)propyl, 4-(3-hydroxyphenyl)butyl, 5-(2-hydroxyphenyl)pentyl, 6-(3-hydroxyphenyl)hexyl, 3,4-dihydroxybenzyl, 3,4,5-trihydroxybenzyl, 4-benzyloxybenzyl, 2-(3-benzyloxyphenyl)ethyl, 1-(2-benzyloxyphenyl)ethyl, 3-[2-(2-phenylethoxy)phenyl]propyl, 4-[3-(3-phenylpropoxy)phenyl]butyl, 1,1-dimethyl-2-[4-(4-phenylbutoxy)phenyl]ethyl, 5-[2-(5-phenylpentyloxy)phenyl]pentyl and 6-[3-(6-phenylhexyloxy)phenyl]hexyl groups and the like.

The lower alkylthio group-substituted lower alkyl group can be exemplified by alkylthio group-substituted alkyl groups in which the alkylthio moiety is a straight-chain or branched-chain alkylthio group of 1 to 6 carbon atoms and the alkyl moiety is a straight-chain or branched-chain alkyl group of 1 to 6 carbon atoms, such as methylthiomethyl, 2-(methylthio)ethyl, 1-(ethylthio)ethyl, 3-(propylthio)propyl, 4-(n-butylthio)butyl, 5-(pentylthio)pentyl and 6-(hexylthio)hexyl groups and the like.

The phenyl-lower alkoxy group-substituted lower alkyl group can be exemplified by phenylalkoxy group-substituted alkyl groups in which the alkoxy moiety is a straight-chain or branched-chain alkoxy group of 1 to 6 carbon atoms and the alkyl moiety is a straight-chain or branched-chain alkyl group of 1 to 6 carbon atoms, such as benzyloxymethyl, 2-(2-phenylethoxy)ethyl, 1-(1-phenylethoxy)ethyl, 3-(3-phenylpropoxy)propyl, 4-(4-phenylbutoxy)butyl, 5-(5-phenylpentyloxy)pentyl, 6-(6-phenylhexyloxy)hexyl, (2-methyl-3-phenylpropoxy)methyl and (1,1-dimethyl-2-phenylethoxy)methyl groups and the like.

The lower alkoxycarbonyl-lower alkyl group can be exemplified by alkoxycarbonylalkyl groups in which the alkoxy moiety is a straight-chain or branched-chain alkoxy group of 1 to 6 carbon atoms and the alkyl moiety is a straight-chain or branched-chain alkyl group of 1 to 6 carbon atoms, such as methoxycarbonylmethyl, 3-methoxycarbonylpropyl, ethoxycarbonylmethyl, 4-ethoxycarbonylbutyl, 1-ethoxycarbonylethyl, 1-methoxycarbonylethyl, 6-propoxycarbonylhexyl, 5-isopropoxycarbonylpentyl, 1,1-dimethyl-2-butoxycarbonylethyl, 2-methyl-3-tert-butoxycarbonylpropyl, 2-pentyloxycarbonylethyl and hexyloxycarbonylmethyl groups and the like.

The hydroxyl group-substituted lower alkyl group can be exemplified by straight-chain or branched-chain alkyl groups of 1 to 6 carbon atoms having 1 to 3 hydroxyl groups as the substituent(s), such as hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, 2,3-dihydroxyethyl, 3,4-dihydroxybutyl and 5,6-dihydroxyhexyl groups and the like.

The piperazine derivatives represented by general formulae (1) and (2) according to the present invention can be produced by various processes. Preferable examples of the processes are shown below.

Reaction formula-1

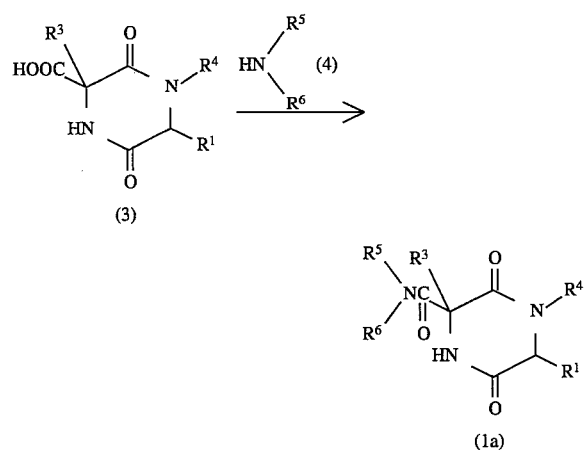

(wherein $R^1$, $R^3$, $R^4$, $R^5$ and $R^6$ are the same as defined above).

The reaction between the compound (3) and the compound (4) is carried out by an ordinary amido bond formation reaction. The amido bond formation reaction can be carried out by various known processes, for example, (a) a mixed acid anhydride process which comprises, for example, reacting the carboxylic acid (3) with an alkyl halocarboxylate and then reacting the resulting mixed acid anhydride with the amine (4), (b) an active ester process which comprises, for example, converting the carboxylic acid (3) into an active ester (e.g. p-nitrophenyl ester, succinimidyl ester or benzotiazol-1-yl ester) and then reacting the active ester with the amine (4), (c) a carbodiimide process which comprises condensing the carboxylic acid (3) and the amine (4) in the presence of an activating agent such as dicyclohexylcarbodiimide, N,N-carbonyldiimidazole or the like, and (d) other processes. The other processes (d) include, for example, a process which comprises converting the carboxylic acid (3) into a carboxylic acid anhydride by the use of a dehydrating agent (e.g. acetic anhydride) and then reacting the carboxylic acid anhydride with the amine (4), and a process which comprises reacting the carboxylic acid (3) with a lower alcohol and then reacting the resulting ester with the amine (4) at a high pressure at a high temperature. There may also be employed a process which comprises activating the carboxylic acid (3) with a phosphorus compound such as triphenylphosphine, diethyl chlorophosphate or the like and then reacting the resulting material with the amine (4). There may also be employed a process which comprises activating the carboxylic acid (3) with an acetylene compound such as trimethylsilylethoxyacetylene or the like and then reacting the resulting material with the amine (4).

In the mixed acid anhydride process (a), the mixed acid anhydride used can be obtained by an ordinary Schotten-Baumann reaction. The anhydride is reacted with the amine (4) generally without being isolated, whereby a compound of general formula (1a) can be produced. The Schotten-Baumann reaction is conducted in the presence of a basic compound. The basic compound is a compound conventionally used in the Schotten-Baumann reaction and includes, for example, organic bases such as triethylamine, trimethylamine, pyridine, dimethylaniline, N-methylmorpholine, 4-dimethylaminopyridine, 1,5-diazabicyclo[4.3.0]nonene-5 (DBN), 1,8-diazabicyclo-[5.4.0]undecene-7 (DBU), 1,4-diazabicyclo[2.2.2]octane (DABCO) and the like, and inorganic bases such as sodium hydroxide, potassium hydroxide, potassium carbonate, sodium carbonate, potassium hydrogen carbonate, sodium hydrogen carbonate and the like. The reaction is conducted at −20° C. to 100° C., preferably at 0°–50° C. for about 5 minutes to 10 hours, preferably for about 5 minutes to 2 hours. The reaction of the resulting mixed acid anhydride with the amine (4) is conducted at −20° C. to 150° C., preferably at 10°–50° C. for about 5 minutes to 10 hours, preferably for about 5 minutes to 5 hours. The mixed acid anhydride process (a) is conducted in an appropriate solvent or mixed solvent or in the absence of any solvent. The solvent may be any solvent conventionally used in the mixed acid anhydride process, and can be exemplified by halogenated hydrocarbons such as dichloromethane, chloroform, dichloroethane and the like; aromatic hydrocarbons such as benzene, toluene, xylene and the like; ethers such as diethyl ether, dioxane, diisopropyl ether, tetrahydrofuran, dimethoxyethane and the like; esters such as methyl acetate, ethyl acetate and the like; and aprotic polar solvents such as 1,1,3,3-tetramethylurea, N,N-dimethylformamide, dimethyl sulfoxide, hexamethylphosphoric triamide and the like. The alkyl α-halocarboxylate used in the mixed acid anhydride process (a) includes, for example, methyl chloroformate, methyl bromoformate, ethyl chloroformate, ethyl bromoformate and isobutyl chloroformate. The alkyl halocarboxylate is used in an amount of generally at least 1 mole, preferably about 1–1.5 moles per mole of the amine (4). The carboxylic acid (3) is used in an amount of generally at least 1 mole, preferably about 1–1.5 moles per mole of the amine (4).

The active ester process (b), when, for example, succinimidyl ester is used, is conducted in the presence or absence of a basic compound in an appropriate solvent which does not adversely affect the reaction. To the reaction system may be added a condensation agent such as dicyclohexylcarbodiimide, N,N-carbonyldiimidazole, 1-ethyl-3-(3'-dimethylaminopropyl)carbodiimide or the like. As the basic compound, there can be used any basic compound used in the Schotten-Baumann reaction. There can further be used alkali metal carboxylates such as sodium acetate, sodium benzoate, sodium formate, potassium acetate, lithium benzoate, cesium acetate and the like; alkali metal halides such as potassium fluoride, cesium fluoride and the like; and so forth. Specific examples of the solvent are halogenated hydrocarbons such as dichloromethane, chloroform, dichloroethane and the like; aromatic hydrocarbons such as benzene, toluene, xylene and the like; ethers such as diethyl ether, dioxane, tetrahydrofuran, dimethoxyethane and the like; esters such as methyl acetate, ethyl acetate and the like; aprotic polar solvents such as N,N-dimethylformamide, dimethyl sulfoxide, hexamethylphosphoric triamide and the like; and mixed solvents thereof. The reaction is conducted at 0°–200° C., preferably at 10°–150° C. and is complete in 1 hour to 3.5 days. With respect to the desirable proportions of the amine (4) and the succinimidyl ester, the former is used in an amount of generally at least 1 mole, preferably 1–2 moles per mole of the latter.

A compound (1a) can also be obtained by reacting the carboxylic acid (3) with the amine (4) in the presence of a phosphorus compound as a condensation agent, such as triphenylphosphine-2,2'-dipyridyl disulfide, diethyl chlorophosphate, diphenylphosphinyl chloride, phenyl N-phenylphospharamide chloridate (?), diethyl cyanophosphate, bis(2-oxo-3-oxazolidinyl)phosphinic chloride or the like. As the basic compound, there can be widely used known basic compounds, for example, the basic compounds used in the Schotten-Baumann reaction, sodium hydroxide and potassium hydroxide. As the solvent, there can be cited, for example, the solvents used in the mixed acid anhydride process (a), pyridine, acetone, acetonitrile and mixed solvents of two or more of them. The reaction is conducted generally at about −20° C. to 150° C. preferably at about 0°–100° C. and is complete generally in about 5 minutes to 30 hours. With respect to the desirable amounts of the condensation agent and the carboxylic acid (3), each of them is used in an amount of at least 1 mole, preferably about 1–2 moles per mole of the amine (4).

A compound (1a) can also be obtained by reacting the carboxylic acid (3) with the amine (4) in the presence of a condensation agent. The reaction is conducted in the presence or absence of a catalyst in an appropriate solvent. The solvent can be exemplified by halogenated hydrocarbons (e.g. dichloromethane, dichloroethane, chloroform and carbon tetrachloride), acetonitrile and N,N-dimethylformamide. The catalyst can be exemplified by organic bases (e.g. 4-dimethylaminopyridine and 4-piperidinopyridine), salts (e.g. pyridinium p-tosylate), camphorsulfonic acid and mercury (II) oxide. As the condensation agent, there can be cited, for example, acetylene compounds such as trimethylsilylethoxyacetylene and the like. The condensation agent is used in an amount of generally 1–10 moles, preferably 2–6 moles per mole of the amine (4). The carboxylic acid (3) is used in an amount of generally at least about 1 mole, preferably about 1–2 moles per mole of the amine (4). The reaction is conducted generally at about 0°–150° C., preferably at about room temperature to 100° C. and is complete generally in about 1–10 hours.

The compound (3) as a starting material can be produced, for example, by the following reaction formulae.

Reaction formula-2

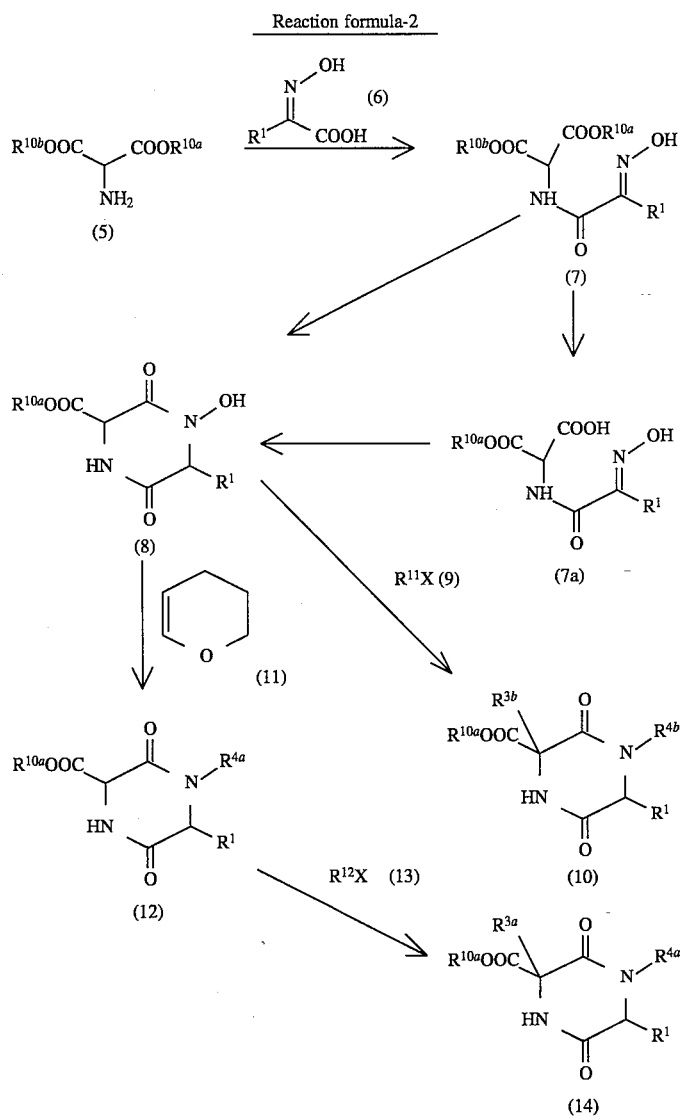

(wherein $R^1$ is the same as defined above; $R^{10a}$ and $R^{10b}$ are each a lower alkyl group; $R^{3a}$ is a lower alkyl group or a phenyl-lower alkyl group; $R^{3b}$ is a phenyl-lower alkyl group; $R^{4a}$ is a tetrahydropyranyloxy group; $R^{4b}$ is a phenyl-lower alkoxy group; X is a halogen atom; $R^{11}$ is a phenyl-lower alkyl group; and $R^{12}$ is a lower alkyl group or a phenyl-lower alkyl group).

The reaction of the compound (5) with the compound (6) is conducted under the same conditions as in the reaction of the compound (3) with the compound (4) in the Reaction formula-1. The reaction for converting the compound (7) into a compound (7a) is conducted under the same conditions as in the reaction for converting the compound (20) into a compound (21) in the Reaction formula-6 to be described later.

The reaction for converting the compound (7) or (7a) into a compound (8) is conducted by first reducing the compound (7) or (7a) in the presence of an acid in an appropriate solvent and then subjecting the reduction product to cyclization. The solvent to be used in the reducing reaction can be exemplified by water, acetic acid, lower alcohols (e.g. methanol, ethanol and isopropanol) and ethers (e.g. tetrahydrofuran, diethyl ether, dioxane and diglyme). The acid can be exemplified by mineral acids (e.g. hydrochloric acid) and organic acids (e.g. acetic acid). The reducing agent can be exemplified by hydride reducing agents such as borane-trimethylamine, sodium cyanoborohydride (?) and the like. The amount of the hydride reducing agent used is at least 1 mole, preferably 1–2 moles per mole of the compound (7) or (7a). The reaction is conducted generally at 0°–100° C., preferably at about 0°–70° C. and is complete in about 1–30 hours.

The subsequent cyclization is conducted in an appropriate solvent. The solvent can be the same as used in the reaction of the carboxylic acid (3) halide with the amine (4). The reaction is conducted generally at room temperature to 200° C., preferably at about 50–150° C. and is complete in about 0.5–10 hours.

The reaction of the compound (8) with the compound (11) is conducted in the presence of an acid in an appropriate solvent. The solvent can be exemplified by halogenated hydrocarbons such as dichloromethane, chloroform, carbon tetrachloride and the like; ethers such as diethyl ether, tetrahydrofuran, dioxane, ethylene glycol monomethyl ether and the like; aromatic hydrocarbons such as benzene, toluene, xylene and the like; esters such as methyl acetate, ethyl acetate and the like; ketones such as acetone, methyl ethyl ketone and the like; polar solvents such as acetonitrile, N,N-dimethylformamide, dimethyl sulfoxide, hexamethylphosphoric triamide and the like; and mixed solvents thereof. The acid can be exemplified by mineral acids (e.g. hydrochloric acid, sulfuric acid and hydrobromic acid) and organic acids (e.g. p-toluenesulfonic acid). The desirable amount of the compound (11) used is generally at least 1 mole, preferably 1–2 moles per mole of the compound (8). The reaction is conducted generally at 0–100° C., preferably at about 0°–70° C. and is complete generally in about 0.5–10 hours.

The reaction of the compound (8) with the compound (9) is conducted in the presence of a basic compound in an appropriate solvent. The solvent can be exemplified by water; lower alcohols such as methanol, ethanol, propanol and the like; ethers such as diethyl ether, tetrahydrofuran, dioxane, ethylene glycol monomethyl ether and the like; aromatic hydrocarbons such as benzene, toluene, xylene and the like; ketones such as methyl acetate, ethyl acetate and the like; ketones such as acetone, methyl ethyl ketone and the like; polar solvents such as acetonitrile, N,N-dimethylformamide, dimethyl sulfoxide, hexamethylphosphoric triamide and the like; and mixed solvents thereof. The basic compound can be exemplified by inorganic bases such as sodium hydroxide, potassium hydroxide, sodium carbonate, potassium carbonate, sodium hydrogen carbonate, potassium hydrogen carbonate, sodium hydride and the like; alkali metals such as sodium, potassium and the like; alkali metal alcoholates such as sodium ethylate, sodium methylate and the like; and organic bases such as triethylamine, pyridine, N,N-dimethylaniline, N-methylmorpholine, 4-methylaminopyridine, DBN, DBU, DABCO and the like. The compound (9) is used in an amount of generally at least 1 mole, preferably 1–5 moles per mole of the compound (8). The reaction is conducted generally at 0°–150° C., preferably at about 0°–100° C. and is complete generally in about 0.5–20 hours.

The reaction of the compound (12) with the compound (13) is conducted under the same conditions as in the reaction of the compound (8) with the compound (9).

Reaction formulae-3

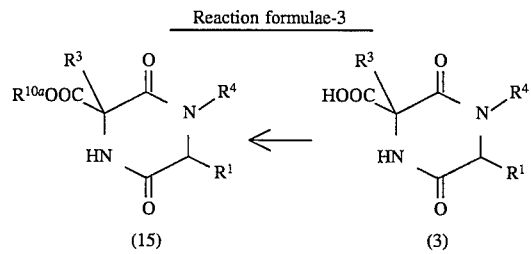

(wherein $R^1$, $R^3$, $R^4$ and $R^{10a}$ are the same as defined above).

The reaction for converting the compound (15) into a compound (3) is conducted by ordinary hydrolysis. Specifically, the hydrolysis can be conducted in the presence of an acid such as mineral acid (e.g. sulfuric acid, hydrochloric acid or nitric acid), organic acid (e.g. acetic acid or aromatic sulfonic acid) or the like, or a basic compound such as sodium carbonate, potassium carbonate, sodium hydroxide, potassium hydroxide, barium hydroxide or the like, in a solvent such as water, alcohol (e.g. methanol, ethanol or isopropyl alcohol), ketone (e.g. acetone or methyl ethyl ketone), ether (e.g. dioxane or ethylene glycol dimethyl ether), acetic acid or mixed solvent thereof. The reaction proceeds generally at about 0°–200° C., preferably at about room temperature to 150° C. and is complete generally in about 0.5–15 hours.

A compound (1), a compound (1a) and a compound (10), wherein $R^4$ and/or $R^{4b}$ is a hydroxyl group, can be produced by reducing a compound (1), a compound (1a) and a compound (10), wherein $R^4$ and/or $R^{4b}$ is a phenyl-lower alkoxy group. This reduction can be conducted, for example, by subjecting the material compound to catalytic hydrogenation in the presence of a catalyst in an appropriate solvent. As the solvent, there can be cited, for example, water; acetic acid; alcohols such as methanol, ethanol, isopropanol and the like; hydrocarbons such as hexane, cyclohexane and the like; ethers such as dioxane, tetrahydrofuran, diethyl ether, ethylene glycol dimethyl ether and the like; esters such as ethyl acetate, methyl acetate and the like; aprotic polar solvents such as dimethylformamide and the like; and mixed solvents thereof. As the catalyst, there can be cited, for example, palladium, palladium black, palladiumcarbon, platinum, platinum oxide, copper chromite and Raney nickel. The desirable amount of the catalyst used is generally about 0.02–1 time by weight of the starting material. The reaction temperature is generally about –20° C. to 100° C., preferably about 0°–80° C.; the hydrogen pressure is generally 1–10 atm.; and the reaction is complete generally in about 0.5–20 hours.

A compound (1), a compound (1a) and a compound (10), wherein $R^4$ and/or $R^{4b}$ is a hydroxyl group, can be produced by hydrolyzing a compound (1), a compound (1a) and a compound (10), wherein $R^4$ and/or $R^{4b}$ is a tetrahydropyranyloxy group. This hydrolysis is conducted in the presence of an acid in an appropriate solvent or without using any solvent. The solvent Can be any solvent which does not adversely affect the reaction, and there can be cited, for example, water; halogenated hydrocarbons such as dichloromethane, chloroform and the like; lower alcohols such as methanol, ethanol, isopropanol and the like; ketones such as acetone, methyl ethyl ketone and the like; ethers such as dioxane, tetrahydrofuran, ethylene glycol monomethyl ether, ethylene glycol dimethyl ether and the like; fatty acids such as formic acid, acetic acid and the like; and mixed solvents thereof. As the acid, there can be cited, for example, mineral acids such as hydrochloric acid, sulfuric acid, hydrobromic acid and the like; and organic acids such as formic acid, trifluoroacetic acid, acetic acid, aromatic sulfonic acid and the like. The amount of the acid used has no particular restriction and can be appropriately selected from a wide range, but desirably is equimolar to a large excess relative to the raw material, preferably about 10–20 moles per mole of the raw material. The reaction proceeds favorably generally at about 0°–200° C. preferably at about room temperature to 150° C. and is complete generally in about 5 minutes to 5 hours.

Reaction formula-4

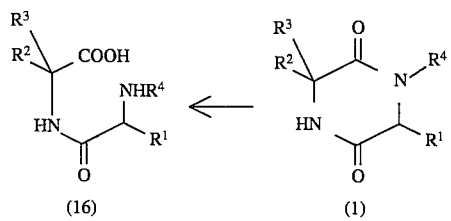

(wherein $R^1$, $R^2$, $R^3$ and $R^4$ are the same as defined above).

The reaction for converting the compound (16) into a compound (1) is conducted under the same conditions as in the reaction of the compound (3) with the compound (4) in the Reaction formula-1.

The compound (16) used as a starting material can be produced, for example, by a process shown by the following reaction formula.

Reaction formula-5

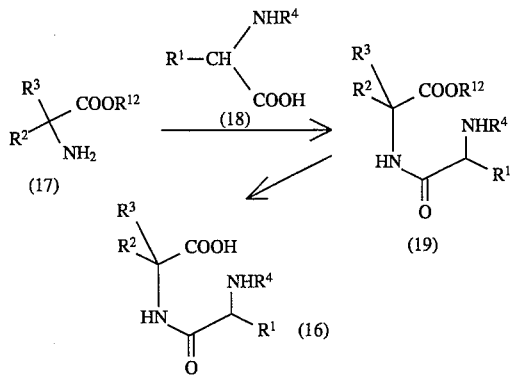

(wherein $R^1$, $R^2$, $R^3$ and $R^4$ are the same as defined above; and $R^{12}$ is a hydrogen atom, a lower alkyl group or a lower alkyl group-containing silyl group).

The reaction of the compound (17) with the compound (18) is conducted under the same conditions as in the reaction of the compound (3) with the compound (4) in the Reaction formula-1.

The reaction for converting the compound (19) into a compound (16), when $R^{12}$ is a lower alkyl group, can be conducted under the same conditions as in the reaction for converting the compound (15) into a compound (3) in the reaction formula-3. Also, said reaction, when $R^{12}$ is a lower alkyl group-containing silyl group, can be conducted under the same conditions as in the reaction for converting a compound (1) wherein $R^4$ is a tetrahydropyranyloxy group, into a compound (1) wherein $R^4$ is a hydroxyl group.

Reaction formula-6

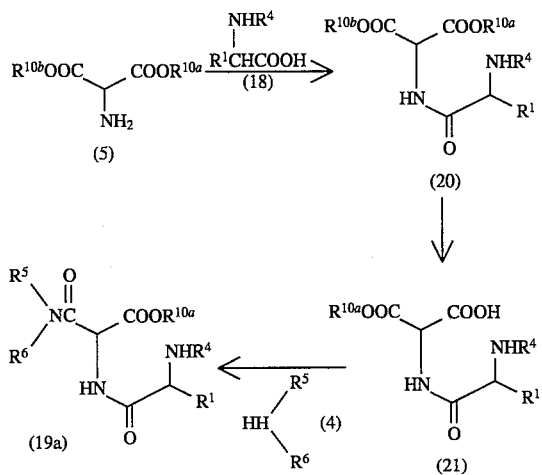

(wherein $R^1$, $R^4$, $R^5$, $R^6$, $R^{10a}$ and $R^{10b}$ are the same as defined above).

The reaction of the compound (5) with the compound (18) is conducted under the same conditions as in the reaction of the compound (3) with the compound (4) in the Reaction formula-1. The reaction for converting the compound (20) into a compound (21) is conducted under the same conditions as in the reaction for converting the compound (15) into a compound (3) in the Reaction formula-3. In this reaction, however, the amount of the basic compound used is preferably 1 mole per mole of the compound (20). The reaction of the compound (21) with the compound (4) is conducted under the same conditions as in the reaction of the compound (3) with the compound (4) in the Reaction formula-1.

Reaction formula-7

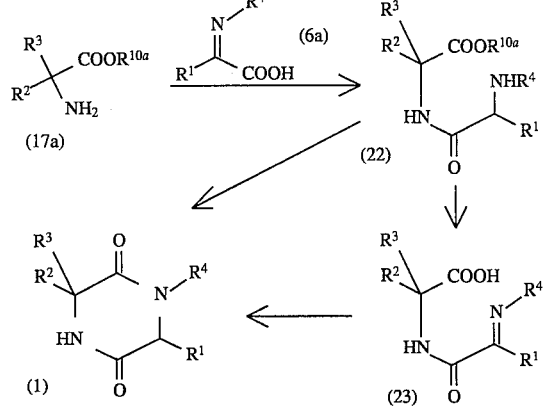

(wherein $R^1$, $R^2$, $R^3$, $R^4$ and $R^{10a}$ are the same as defined above).

The reaction of the compound (17a) with the compound (6a) is conducted under the same conditions as in the reaction of the compound (5) with the compound (6) in the Reaction formula-2. The reaction for converting the compound (22) into a compound (23) is conducted under the same conditions as in the reaction for converting the compound (15) into a compound (3) in the Reaction formula-3. The reaction for converting the compound (22) into a compound (1) and the reaction for converting the compound (23) into a compound (1) are both conducted under the same conditions as in the reaction for converting the compound (7) into a compound (8) in the Reaction formula-2.

Reaction formula-8

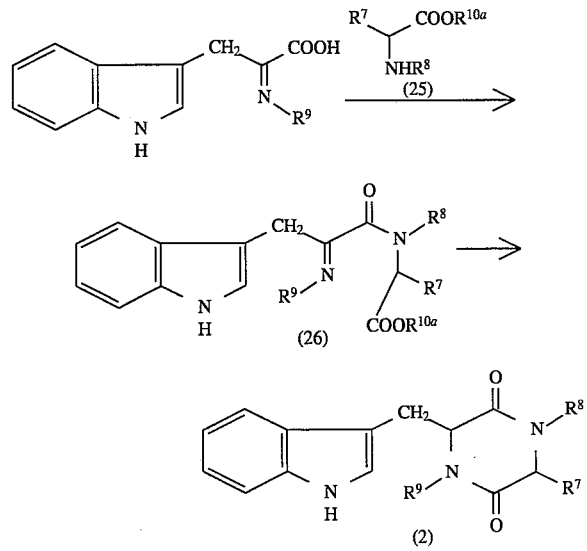

(wherein $R^7$, $R^8$, $R^9$ and $R^{10a}$ are the same as defined above).

The reaction of the compound (24) with the compound (25) is conducted under the same conditions as in the reaction of the compound (3) with the compound (4) in the Reaction formula-1. The reaction for converting the compound (26) into a compound (2) is conducted under the same conditions as in the reaction for converting the compound (7) into a compound (8) in the Reaction formula-2.

Reaction formula-9

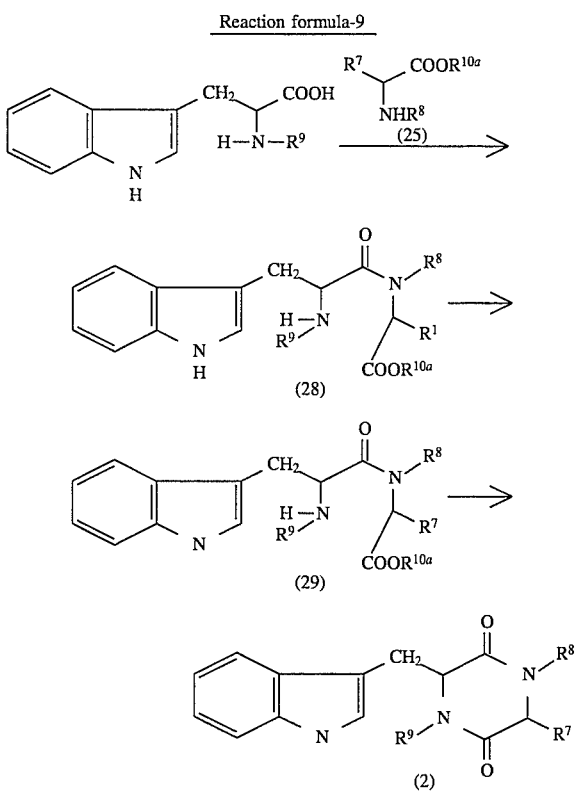

(wherein $R^7$, $R^8$, $R^9$ and $R^{10a}$ are the same as defined above).

The reaction of the compound (27) with the compound (25) is conducted under the same conditions as in the reaction of the compound (3) with the compound (4) in the Reaction formula-1. The reaction for converting the compound (28) into a compound (29) is conducted under the same conditions as in the reaction for converting the compound (15) into a compound (3) in the Reaction formula-3. The reaction for converting the compound (29) into a compound (2) is conducted under the same conditions as in the reaction of the compound (3) with the compound (4) in the Reaction formula-1.

A compound (2) wherein $R^9$ is a hydroxyl group, can be produced by reducing a compound (2) wherein $R^9$ is a phenyl-lower alkoxy group. This reduction is conducted under the same conditions as in the reduction of a compound (1) wherein $R^4$ is a phenyl-lower alkoxy group.

A compound (1) wherein $R^2$, $R^5$ or $R^6$ is a phenyl-lower alkyl group having at least one hydroxyl group as the substituent(s) on the phenyl ring, can be produced by reducing a compound (1) wherein $R^2$, $R^5$ or $R^6$ is a phenyl-lower alkyl group having at least one phenyl-lower alkoxy group as the substituent(s) on the phenyl ring. A compound (2) wherein $R^7$ is a phenyl-lower alkyl group having at least one hydroxyl group as the substituent(s) on the phenyl ring, or is a hydroxyl group-substituted lower alkyl group, can be produced by reducing a compound (2) wherein $R^7$ is a phenyl-lower alkyl group having at least one phenyl-lower alkoxy group as the substituent(s) on-the phenyl ring, or is a phenyl-lower alkoxy group-substituted lower alkyl group. These reductions are conducted under the same conditions as in the reduction of a compound (1) wherein $R^4$ is a phenyl-lower alkoxyl group.

Of the present compounds represented by general formulae (1) and (2), those having a basic group can each be made into an acid addition salt easily by being reacted with a pharmacologically acceptable acid. As the acid, there can be cited, for example, inorganic acids such as hydrochloric acid, sulfuric acid, phosphoric acid, hydrobromic acid and the like; and organic acids such as oxalic acid, acetic acid, succinic acid, malonic acid, methanesulfonic acid, maleic acid, fumaric acid, malic acid, tartaric acid, citric acid, benzoic acid and the like.

Of the present compounds represented by general formulae (1) and (2), those having an acidic group can each be made into a salt easily by being reacted with a pharmacologically acceptable basic compound. As the basic compound, there can be cited, for example, sodium hydroxide, potassium hydroxide, calcium hydroxide, sodium carbonate, potassium hydrogen carbonate and the like.

Each of the intended compounds obtained by the above reaction formulas can be easily separated from the reaction system and purified by ordinary means. The means for separation can be exemplified by solvent extraction, dilution, recrystallization, column chromatography and preparative thin-layer chromatography.

Needless to say, the present compounds include optical isomers and stereoisomers.

Each of the compounds of general formulae (1) and (2) is used generally in the form of ordinary pharmaceutical preparation. The pharmaceutical preparation is prepared by using diluents or excipients ordinarily used, such as filler, bulking agent, binder, humectant, disintegrator, surfactant, lubricant and the like. The pharmaceutical preparation can be prepared in various forms depending upon the purpose of remedy, and the typical forms include tablets, pills, a powder, a solution, a suspension, an emulsion, granules, capsules, suppositories, an injection (e.g. solution or suspension), etc. In preparing tablets, there can be used various carriers known in the art, exemplified by excipients such as lactose, white sugar, sodium chloride, glucose, urea, starch, calcium carbonate, kaolin, crystalline cellulose, silicic acid and the like; binders such as water, ethanol, propanol, simple syrup, glucose solution, starch solution, gelatin solution, carboxymethyl cellulose, shellac, methyl cellulose, potassium phosphate, polyvinylpyrrolidone and the like; disintegrators such as dry starch, sodium alginate, powdered agar, powdered laminarin, sodium hydrogen carbonate, calcium carbonate, polyoxyethylene sorbitan-fatty acid esters, sodium lauryl sulfate, stearic acid monoglyceride, starch, lactose and the like; disintegration inhibitors such as white sugar, stearin, cacao butter, hydrogenated oil and the like; absorption promoters such as quaternary ammonium salts, sodium lauryl sulfate and the like; humectants such as glycerine, starch and the like; adsorbents such as starch, lactose, kaolin, bentonite, colloidal silicic acid and the like; and lubricants such as refined talc, stearic acid salts, boric acid powder, polyethylene glycol and the like.

The tablets can be prepared, as necessary, in the form of ordinary coated tablets, such as sugar-coated tablets, gelatin-coated tablets, enteric coated tablets or film-coated tablets, or in the form of double-layered tablets or multi-layered tablets. In preparing pills, there can be used various carriers known in the art, exemplified by excipients such as glucose, lactose, starch, cacao butter, hardened vegetable oils, kaolin, talc and the like; binders such as powdered acacia, powdered tragacanth, gelatin, ethanol and the like; and disintegrators such as laminarin, agar and the like. In preparing suppositories, there can be used various known carriers exemplified by a polyethylene glycol, cacao butter, a higher alcohol, a higher alcohol ester, gelatin and a semi-synthetic glyceride. In preparing an injection (solution, emulsion or suspension), the solution and the suspension are sterilized and are preferably made isotonic to the blood. In preparing the solution, emulsion-or suspension, there can be used all diluents conventionally used in the art, such as water, ethyl alcohol, propylene glycol, ethoxylated isostearyl alcohol, polyoxyisostearyl alcohol and polyoxyethylene sorbitan-fatty acid esters. In this case, the injection may contain sodium chloride, glucose or glycerine in an amount sufficient to make the injection isotonic, and may further contain a solubilizing agent, a buffer solution, a soothing agent, etc. all ordinarily used. The pharmaceutical preparation may furthermore contain, as necessary, a coloring agent, a preservative, a perfume, a flavoring agent, a sweetening agent and other drugs.

The amount of the compounds of general formulae (1) and (2) to be contained in the pharmaceutical preparation is not particularly restricted and can be appropriately selected from a wide range, but the amount is generally 1–70% by weight, preferably 1–30% by weight in the pharmaceutical preparation.

The method for administering the pharmaceutical preparation is not particularly restricted. It is decided depending upon the form of preparation, the age, distinction of sex and other conditions of patient, the disease condition of patient, etc. For example, tablets, pills, a solution, a suspension, an emulsion, granules or capsules are administered orally. An injection is intravenously administered singly or in admixture with an ordinary auxiliary solution of glucose, amino acids or the like, or, as necessary, is singly administered intramuscularly, intradermally, subcutaneously or intraperitoneally. Suppositories are administered intrarectally.

The dose of the pharmaceutical preparation is appropriately selected depending upon the administration method, the age, distinction of sex and other conditions of patient, the disease condition of patient, etc., but the desirable dose is generally about 0.5–30 mg per kg of body weight per day in terms of the amount of the active ingredient, i.e. the compounds of general formulae (1) and (2). The desirable content of the active ingredient in each unit of administration form is about 10–1,000 mg.

The present invention is described more specifically below with reference to Preparation Example, Reference Examples, Examples and Pharmacological Tests.

| Preparation Example 1 | |
|---|---|
| (3RS,6RS)-3-(3,5-di-tert-butyl-4-hydroxy-benzyl)-1-hydroxy-6-isobutylpiperazine-2,5-dione | 150.0 g |
| Citric acid | 1.0 g |
| Lactose | 33.5 g |
| Dicalcium phosphate | 70.0 g |
| Pluronic F-68 (trademark for a polyoxyalkylene glycol manufactured by BASF-Wyandott Corp., N.J., U.S.A.) | 30.0 g |
| Sodium laurylsulfate | 15.0 g |
| Polyvinylpyrrolidone | 15.0 g |
| Carbowax 1500 (trademark for a polyethylene glycol manufactured by Union Carbide Corp., N.Y., U.S.A.) | 4.5 g |
| Carbowax 6000 (trademark for a polyethylene glycol manufactured by Union Carbide Corp., N.Y., U.S.A.) | 45.0 g |
| Corn starch | 30.0 g |
| Dried sodium laurylsulfate | 3.0 g |
| Dried magnesium stearate | 3.0 g |
| Ethanol | q.s. |

The present compound, citric acid, lactose, dicalcium phosphate, Pluronic F-68 and sodium laurylsulfate were mixed.

The mixture was sieved through a screen of No. 60, and the sieved material was subjected to wet granulation with an ethanolic solution containing polyvinylpyrrolidone, Carbowax 1500 and Carbowax 6000. As necessary, ethanol was added and the resulting material was made into a paste-like lump. Corn starch was added to this lump and mixing was continued until granules of uniform particle size were formed. The granules were sieved through a screen of No. 10, and the sieved granules were placed on a tray and dried in an oven at 100° C. for 12–14 hours. The dried granules were sieved through a screen of No. 16, and to the sieved granules were added dried sodium laurylsulfate and dried magnesium stearate. The whole mixture was mixed well and was compressed into a desired form by using a tablet machine, to obtain tablets each to be used as the core portion of a coated tablet.

The core portions were treated with a varnish, and the treated surfaces thereof were coated with talc for preventing the surfaces from moisture adsorption. The resulting surfaces of core portions were further coated with a primary coating and further coated with a varnish a plurality of times necessary for oral administration. In order to obtain final tablets having a completely spherical shape with a smooth surface, the coated tablets were further coated with a primary coating and a smoothening agent. The resulting tablets were coated with a coloring agent until the surfaces had a desired color. After the coated tablets were dried, the surfaces thereof were polished to prepare tablets having a uniform gloss.

REFERENCE EXAMPLE 1

240 ml of 7N hydrochloric acid (an ethanolic solution) was dropwise added to 240 ml of an ethanolic solution containing 18.46 g of diethyl N-(2-hydroxyimino-4-methylpentanoyl)aminomalonate and 5.49 g of borane-trimethylamine, with ice-cooling. The mixture was stirred at room temperature for 15 hours. The reaction mixture was subjected to vacuum distillation at room temperature to remove the solvent. The residue was dissolved in dichloromethane. The resulting solution was washed with an aqueous solution saturated with sodium chloride and an aqueous solution saturated with sodium hydrogen carbonate in this order, then dried with anhydrous magnesium sulfate, and was subjected to distillation to remove the solvent. The resulting yellow oily substance was dissolved in 120 ml of toluene. The solution was refluxed for 1 hour and then subjected to distillation to remove the solvent. 19.02 g of the resulting orange oily substance was purified by silica gel column chromatography (eluant: dichloromethane/methanol =30/1) to obtain 2.94 g of 3-ethoxycarbonyl-1-hydroxy-6-isobutylpiperazine-2,5-dione as an orange oily substance.

$^1$H-NMR (DMSO-$d_6$, 250 MHz) δ ppm: 0.87 (3H, d, J=6.5 Hz), 0.88 (3H, d, J=6.5 Hz), 1.20 (1.4H, d, J=7 Hz), 1.21 (0.6H, d, J=7 Hz), 1.60–1.85 (2H, m), 1.85–2.05 (1H, m), 4.01 (1H, t, J=6.5 Hz), 4.16 (2H, q, J=7 Hz), 4.65 (0.7H, d, J=3.5 Hz), 4.82 (0.3H, s), 8.56 (0.7H, d, J=8 Hz), 8.60 (0.3H, brs), 10.30 (1H, brs)

REFERENCE EXAMPLE 2

7.60 g of potassium carbonate and 6.3 ml of benzyl chloride were added to 100 ml of a solution of 9.57 g of 3-ethoxycarbonyl-1-hydroxy-6-isobutylpiperazine-2,5-dione in anhydrous N,N-dimethylformamide, on ice-cooling. The mixture was stirred at room temperature for 16 hours. The reaction mixture was diluted with 450 ml of ethyl acetate, then washed three times with an aqueous solution saturated with sodium chloride, and dried with anhydrous magnesium sulfate. The resulting solution was subjected to distillation to remove the solvent. The residue was allowed to stand. The resulting crystals were collected by filtration and washed with methanol to obtain 4.51 g of (3RS,6SR)-3-benzyl-1-benzyloxy-3-ethoxycarbonyl-6-isobutylpiperazine-2,5-dione as colorless columnar crystals.

$^1$H-NMR (CDCl$_3$, 250 MHz) δ ppm: 0.80 (3H, d, J=6.5 Hz), 0.81 (3H, d, J=6.5 Hz), 1.32 (3H, t, J=7 Hz), 1.60–1.80 (2H, m), 1.80 2.00 (1H, m), 3.32, 3.65 (each 1H, d, J=14 Hz), 3.59 (1H, dd, J=6 Hz, 7 Hz), 4.29 (2H, q, J=7 Hz), 4.51, 4.80 (each 1H, d, J=10.5 Hz), 6.55–6.95 (1H, br), 7.06 (2H, d, J=7 Hz), 7.20 7.50 (8H, m)

REFERENCE EXAMPLE 3

5.3 ml of 1N sodium hydroxide was added to 25 ml of a suspension of 2.32 g of (3RS,6SR)-3-benzyl-1-benzyloxy-3-ethoxycarbonyl-6-isobutylpiperazine-2,5-dione in ethanol. The mixture was stirred at room temperature for 1.5 hours. The reaction mixture was adjusted to pH 3 with 1N hydrochloric acid. Thereto were added 80 ml of ethyl acetate and 80 ml of water to conduct distribution. The organic layer was dried with anhydrous magnesium sulfate and then subjected to vacuum distillation to remove the solvent at room temperature to obtain 2.17 g of (3RS,6SR)-3-benzyl-1-benzyloxy-3-carboxy-6-isobutylpiperazine-2,5-dione as a light yellow solid.

$^1$H-NMR (DMSO-d$_6$, 250 MHz) δ ppm: 0.70 (3H, d, J=6.5 Hz), 0.71 (3H, d, J-6.5 Hz), 1.50–1.65 (2H, m), 1.65–1.85 (1H, m), 3.07, 3.53 (each 1H, d, J=13.5 Hz), 3.43 (1H, t, J-6 Hz), 4.34, 4.58 (each 1H, d, J=10.5 Hz), 6.94 (2H, d, J=6.5 Hz), 7.10–7.45 (9H, m), 8.87 (1H, brs)

By using suitable starting materials and by employing the same manner as in Reference Example 3, there was obtained the following compound. (3RS,6SR)-3-Carboxy-6-isobutyl-3-methyl-1-(2-tetrahydropyranyloxy)piperazine-2,5-dione Brown oily substance $^1$H-NMR (CDCl$_3$, 250 MHz) δ ppm: 0.96 (3H, d, J=6 Hz), 0.97 (3H, d, J=6 Hz), 1.45–2.00 (9H, m), 1.78 (1.5H, s), 1.83 (1.5H, s), 3.55–3.75 (1H, m), 3.80–3.95 (1H, m), 4.50–4.70 (1H, m), 5.05–5.20 (1H, m), 6.71 (2H, brs)

REFERENCE EXAMPLE 4

0.45 g of p, toluenesulfonic acid hydrate was added to 60 ml of a solution of 6.15 g of 3-ethoxycarbonyl-1-hydroxy-6-isobutylpiperazine-2,5-dione and 4 ml of 3,4-dihydro-2H-pyran in anhydrous dichloromethane. The mixture was stirred at room temperature for 4 hours. The reaction mixture was washed with an aqueous solution saturated with sodium hydrogen carbonate and then dried with anhydrous magnesium sulfate. The resulting mixture was subjected to distillation to remove the solvent to obtain 9.67 g of 3-ethoxycarbonyl-6-isobutyl-1-(2-tetrahydropyranyloxy)piperazine-2,5-dione as an orange oily substance.

$^1$H-NMR (CDCl$_3$, 250 MHz) δ ppm: 0.97 (3H, t, J=7 Hz), 0.98 (3H, t, J=7 Hz), 1.33 (3H, t, J=7 Hz), 1.45–1.95 (9H, m), 3.55–3.70 (1H, m), 3.80–3.95 (1H, m), 4.20–4.40 (2H, m), 4.5–4.60 (1H, m), 4.65–4.80 (1H, m), 5.15–5.22 (1H, m), 6.72 (1H, brs)

REFERENCE EXAMPLE 5

1.04 g of 60% sodium hydride was added to 100 ml of 9.67 g of 3-ethoxycarbonyl-6-isobutyl-1-(2-tetrahydropyranyloxy)piperazine-2,5-dione in anhydrous N,N-dimethylformamide, on ice cooling, and the mixture was stirred for 10 minutes. Thereto was added 3.5 ml of methyl iodide. The mixture was stirred at room temperature for 5 hours. The reaction mixture was ice-cooled and poured into an aqueous solution saturated with ammonium chloride. The mixture was extracted with ethyl acetate. The extract was washed three times with an aqueous solution saturated with sodium chloride, dried with anhydrous magnesium sulfate, and subjected to distillation to remove the solvent to obtain 8.53 g of (3RS,6SR)-3-ethoxycarbonyl-6-isobutyl-3-methyl-1-(2-tetrahydropyranyloxy)piperazine-2,5-dione as a brown oily substance.

$^1$H-NMR (CDCl$_3$, 250 MHz) δ ppm: 0.98 (3H, d, J=6.5 Hz), 0.99 (3H, d, J=6.5 Hz), 1.26 (1.5H, t, J=7 Hz), 1.31 (1.5H, t, J=7 Hz), 1.45–1.90 (9H, m), 1.71 (1.5H, s), 1.75 (1.5H, s), 3.60–3.70 (1H, m), 3.85–3.95 (1H, m), 4.25 (2H, q, J=7 Hz), 4.50–4.60 (1H, m), 5.00–5.20 (1H, m)

REFERENCE EXAMPLE 6

14.86 g of dicyclohexylcarbodiimide was added to 200 ml of a solution of 17.07 g of N-benzyloxyleucine and 9.09 g of N-hydroxysuccinimide in anhydrous dioxane. The mixture was stirred at room temperature for 2 hours. The resulting insoluble materials were removed by filtration. To the filtrate was added 28.94 g of ethyl (3', 5'-di-tert-butyl)tyrosinate The mixture was stirred at room temperature for 12 hours. The reaction mixture was diluted with 1,000 ml of ethyl acetate. The resulting solution was washed with 1N hydrochloric acid, an aqueous solution saturated with sodium hydrogen carbonate and an aqueous solution saturated with sodium chloride in this order, then dried with anhydrous magnesium sulfate, and subjected to distillation to remove the solvent. The residue was purified by silica gel column chromatography (eluant: ethyl acetate/n-hexane =1/6 - 1/4) to obtain 34.63 g of ethyl N-(N-benzyloxyleucyl)-(3',5'-di-tert-butyl)tyrosinate as a brown oily substance.

$^1$H-NMR (CDCl$_3$, 250 MHz) δ ppm: 0.75–0.95 (6H, m), 1.22 (1.6H, t, J=7 Hz), 1.26 (0.4H, t, J=7 Hz), 1.30–1.50 (1H, m), 1.39 (14.4H, s), 1.40 (3.6H, s), 1.50–1.70 (1H, m), 3.01, 3.10 (each 1H, dd, J=6 Hz, 14 Hz), 3.35–3.55 (1H, m), 4.05–4.25 (2H, m), 4.43, 4.53 (each 0.2H, d, J=12 Hz), 4.61, 4.71 (each 0.8H, d, J=12 Hz), 4.75–4.95 91H, m), 5.10 (0.2H, s), 5.12 (0.8, s), 5.59 (0.8H, d, J=4.5 Hz), 5.67 (0.2H, d, J=6 Hz), 6.74 (0.2H, d, J=8.5 Hz), 6.91 (1.6H, s), 6.92 (0.4H, s), 7.02 (0.8H, d, J=8.5 Hz), 7.20–7.45 (5H, m)

REFERENCE EXAMPLE 7

By using suitable starting materials and by employing the same manner as in REFERENCE EXAMPLE 6, there were obtained the following compounds.
Ethyl N-(N-benzyloxyleucyl)-(3',5'-dimethoxy)tyrosinate Colorless oily substance $^1$H-NMR (CDCl$_3$, 250 MHz) δ ppm: 0.85, 0.87 (each 2.4H, d, J=6.5 Hz), 0.86, 0.91 (each 0.6H, d, J=6.5 Hz), 1.15–1.50 (5H, m), 1.50–1.65 (1H, m), 3.00–3.20 (2H, m), 3.49 (1H, dd, J=5.5 Hz, J=8 Hz), 3.82 (6H, s), 4.10–4.30 (2H, m), 4.46, 4.56 (each 0.2H, d, J=12 Hz), 4.63, 4.72 (each 0.8H, d, J=1 2 Hz), 4.91 (1H, dt, J=6 Hz, J=98 Hz), 5.46 (1H, brs), 6.35 (1.6H, s), 6.38 (0.4H, s), 6.92 (0.2H, d, J=8 Hz), 7.02 (0.8H, d, J=8 Hz), 7.15–7.50 (5H, m)
Ethyl N-(N-benzyloxyleucyl)-(3',5'-dimethyl)tyrosinate Yellow oily substance $^1$H-NMR (CDCl$_3$, 250 MHz) δ ppm: 0.85, 0.87 (each 0.6H, d, J=6 Hz), 0.86, 0.89 (each 2.4H, d, J=7 Hz), 1.27 (3H, t, J=7 Hz), 1.20–1.45 (2H, m), 1.55–1.70 (1H, m), 2.15

(1.2H, s), 2.17 (4.8H, s), 2.90–3.15 (2H, m), 3.40–3.55 (1H, m), 4.10 (2H, q, J=7 Hz), 4.64, 4.74 (each 1H, d, J=12 Hz), 4.86 (1H, dt, J=5.5 Hz, J=8 Hz), 5.66 (1H, brs), 6.73 (1.6H, s), 6.76 (0.4H, s), 6.81 (0.2H, d, J=9.5 Hz), 7.00 (0.8H, d, J=8 Hz), 7.20–7.45 (5H, m)

REFERENCE EXAMPLE 8

13.2 ml of triethylamine and 6 ml of trimethylsilyl chloride were added to 150 ml of a suspension of 11.78 g of (2',4'-dimethoxy)phenylalanine hydrochloride in anhydrous dichloromethane, in a nitrogen atmosphere. The mixture was refluxed for 1.5 hours. Separately, 9.28 g of dicyclohexylcarbodiimide was added to 100 ml of a solution of 10.68 g of N-benzyloxyleucine and 5.18 g of N-hydroxysuccinimide in anhydrous dioxane. The mixture was stirred at room temperature for 2 hours. The resulting insoluble materials were removed by filtration. The filtrate was added to the above reaction mixture after refluxing, at room temperature. The resulting mixture was stirred for 12 hours. The reaction mixture was diluted with 1,200 ml of ethyl acetate. The resulting solution was washed with 1N hydrochloric acid, an aqueous solution saturated with sodium chloride, an aqueous solution saturated with sodium hydrogen carbonate and an aqueous solution saturated with sodium chloride in this order, then dried with anhydrous magnesium sulfate, and subjected to vacuum distillation to remove the solvent to obtain 17.40 g of N-(N-benzyloxyleucyl)-(2',4'-dimethoxy)phenylalanine as a light brown vitreous substance.

$^1$H-NMR (CDCl$_3$, 250 MHz) δ ppm: 0.82, 0.85 (each 1.5H, d, J=6.5 Hz), 0.87, 0.92 (each 1.5H, d, J=6.5 Hz), 1.05–1.30 (2H, m), 1.45–1.60 (1H, m), 3.05–3.02 (1H, m), 3.35–3.55 (1H, m), 3.74 (3H, s), 3.75 (3H, s), 3.90–4.05 (0.5H, m), 4.10–4.25 (0.5H, m), 4.50–4.80 (3H, m), 6.30–6.50 (2H, m), 7.01 (1H, d, J=8 Hz), 7.15–7.40 (5H, m)

By using suitable starting materials and by employing the same manner as in Reference Example 8, there was obtained the compound of Reference Example 9 described below.

REFERENCE EXAMPLE 9

64 ml of a 2N aqueous sodium hydroxide solution was added to a solution of 34.63 g of ethyl N-(N-benzyloxyleucyl)-(3',5'-di-tert-butyl)tyrosinate in ethanol. The mixture was stirred at room temperature for 1.5 hours. The reaction mixture was adjusted to pH 1 with concentrated hydrochloric acid. Thereto was added 500 ml of water. The mixture was extracted with ethyl acetate twice. The extract was washed with an aqueous solution saturated with sodium chloride, then dried with anhydrous magnesium sulfate, and subjected to vacuum distillation to remove the solvent to obtain 32.83 g of N-(N-benzyloxyleucyl)-(3',5'-di-tert-butyl)tyrosine as a brown oily substance.

$^1$H-NMR (CDCl$_3$, 250 MHz) δ ppm: 0.82 (3H, d, J=6.5 Hz), 0.84 (3H, d, J=6.5 Hz), 1.10–1.37 (2H, m), 1.39 (18H, s), 1.45–1.65 (1H, m), 2.99 (0.43H, dd, J=7 Hz, J=14 Hz), 3.16 (0.43H, dd, J=5.5 Hz, J=14 Hz), 3.04–3.28 (0.15H, m), 3.42 (0.15H, dd, J=6 Hz, J=8 Hz), 3.51 (0.85H, dd, J=5 Hz, J=9 Hz), 4.35, 4.42 (each 0.15H, d, J=12 Hz), 4.53, 4.60 (each 0.85H, d, J=12 Hz), 4.70–4.90(1H, m), 5.13 brs), 6.94 (2H, s), 6.96 (1H, d, J=9 Hz), 7.15–7.45 (5H, m)

By using suitable starting materials and by employing the same manner as in Reference Example 9, there was obtained the compound of Reference Example 8.

REFERENCE EXAMPLE 10

By using suitable starting materials and by employing the same manners as in Reference Examples 8 and 9, there were obtained the following compounds.

N-(N-Benzyloxyleucyl)-(3',5'-dimethoxy)tyrosine Colorless oily substance $^1$H-NMR (CDCl$_3$, 250 MHz) δ ppm: 0.83 (3H, d, J=6 Hz), 0.85 (3H, d, J=6 Hz), 1.15–1.45 (2H, m), 1.45–1.65 (1H, m), 3.04 (1H, dd, J=6.5 Hz, J=14 Hz), 3.16 (1H, dd, J=5.5 Hz, J=14 Hz), 3.52 (1H, dd, J=5.5 Hz, J=8.5 Hz), 3.79 (3H, s), 3.80 (3H, s), 4.40, 4.48 (each 0.2H, d, J=12 Hz), 4.75–5.00 (1H, m), 6.39 (1.6H, s), 6.42 (0.4H, s), 6.10–6.90 (2H, br), 6.98 (0.2H, d, J=7 Hz), 7.08 (0.8, d, J=7.5 Hz), 7.15–7.40 (5H, m)

N-(N-Benzyloxyleucyl)-(3',5'-dimethyl)tyrosine White solid $^1$H-NMR (DMSO-d$_6$, 250 MHz) δ ppm: 0.80 (3H, d, J=6.5 Hz), 0.86 (3H, d, J=6.5 Hz), 1.30–1.45 (2H, m), 1.50–1.70 (1H, m), 2.03 (6H, s), 2.77 (1H, dd, J-7.5 Hz, J=14 Hz), 2.87 (1H, dd, J=5.5 Hz, J=14 Hz), 3.83 (1H, t, J=8 Hz), 4.44 (1H, dd, J=5 Hz, J=8 Hz), 4.80 (2H, s), 76.70 (2H, s), 7.20–7.40 (5H, m), 8.45 (1H, brs)

(N-Benzyloxy-DL-tryptophyl)-L-serine Brown foam-like substance $^1$H-NMR (DMSO-d$_6$, 250 MHz) δ ppm: 2.80–3.00 (1H, m), 3.00–3.15 (1H, m), 3.45–3.65 (1H, m), 3.65–3.85 (1H, m), 3.90–4.05 (1H, m), 4.30–4.45 (1H, m), 4.67, 4.73 (1H, d, J=11 Hz), 6.97 (1H, t, J=7.5 Hz), 7.07 (1H, t, J=7 Hz), 7.17 (1H, d, J=7 Hz), 7.29 (5H, s), 7.34 (1H, d, J=8 Hz), 7.55 (1H, d, J=8 Hz), 8.21 (1H, d, J=8 Hz), 10.87 (1H, brs)

REFERENCE EXAMPLE 11

26.82 g of dicyclohexylcarbodiimide was added to one liter of a solution of 34.47 g of methyl (3',4',5'-trimethoxy)phenylalaninate, 18.87 of 2-hydroxyimino-4-methylpentanoic acid and 14.96 g of N-hydroxysuccinimide in anhydrous dioxane. The mixture was stirred at room temperature for 18 hours. The reaction mixture was filtered and the filtrate was subjected to distillation to remove the solvent. The residue was purified by silica gel column chromatography (eluant: ethyl acetate/n-hexane=1/2) to obtain 42.70 g of methyl N-(2-hydroxyimino-4-methylpentanoyl)-(3',4',5'-trimethoxy)phenylalaninate. White powder $^1$H-NMR (CDCl$_3$, 250 MHz) δ ppm: 0.90 (6H, d, J=6.5 Hz), 1.90–2.11 (1H, m), 2.52 (2H, d, J=7.5 Hz), 3.02–3.18 (2H, m), 3.74 (3H, s), 3.81 (6H, s), 3.82 (3H, s), 4.91 (1H, dt, J=6 Hz, J=8.5 Hz), 6.32 (2H, s), 7.17 (1H, d, J=8.5 Hz), 7.83 (1H, brs)

REFERENCE EXAMPLE 12

By using suitable starting materials and by employing the same manner as in Reference Examples 11, there were obtained the following compounds.

Ethyl N-(2-hydroxyimino-4-methylpentanoyl)-(3',5'-di-tert-butyl)tyrosinate.

White powder $^1$H-NMR (CDCl$_3$, 250 MHz) δ ppm: 0.90 (6H, d, J=6.5 Hz), 1.21 (3H, t, J=7 Hz), 1.28 (18H, s), 1.80–2.15 (1H, m), 2.52 (2H, d, J=7.5 Hz), 3.00 (1H, dd, J=6 Hz, J=14 Hz), 3.07 (1H, dd, J=6 Hz, J=14 Hz), 4.00–4.23 (2H, m), 4.82 (1H, dt, J=6 Hz, J=8 Hz), 5.10 (1H, s), 6.89 (2H, s), 7.15 (1H, brd, J=8.5 Hz), 7.56 (1H, brs) Methyl N-(2-hydroxyimino-4-methylpentanoyl)-L-phenylalaninate Colorless needle-like crystals Melting point: 71°–73° C.

Methyl N-(2-hydroxyimino-4-methylpentanoyl)-O-benzyl-L-tyrosinate
Colorless needle-like crystals
Melting point: 108°–110° C.
Ethyl N-(2-hydroxyimino-4-methylpentanoyl)-(3',5'-dichloro)-L-tyrosinate
White solid
$^1$H-NMR (CDCl$_3$, 250 MHz) δ ppm: 0.91 (6H, d, J=6.5 Hz), 1.27 (3H, t, J=7 Hz), 1.90–2.10 (1H, m), 2.52 (2H, d, J=7.5 Hz), 2.98 91H, dd, J=6 Hz, J=14 Hz), 3.08 (1H, dd, J=6 Hz, J=14 Hz), 4.20, 4.21 (each 1H, q, J=7 Hz), 4.81 (1H, dt, J=6 Hz, J=8 Hz), 5.86 (1H, s), 7.03 (2H, s), 7.26 (1H, d, J=8 Hz), 8.24 (1H, brs)
Methyl $N^{im}$-Benzyl-N-(2-hydroxyimino-4-methylpentanoyl)-L-histidinate
White solid
$^1$H-NMR (CDCl$_3$, 250 MHz) δ ppm: 0.86 (3H, d, J=6.5 Hz), 0.88 (3H, d, J=6.5 Hz), 1.88–2.10 (1H, m), 2.49 (2H, d, J=7.5 Hz), 3.09 (1H, dd, J=7.5 Hz, J=14.5 Hz), 3.17 (1H, dd, J=6 Hz, J=14.5 Hz), 3.62 (3H, s), 4.87 (1H, dt, J=7 Hz, J=8 Hz), 5.03 (2H, s), 6.77 (1H, s), 7.10–7.23 (2H, m), 7.30–7.46 (3H, m), 7.44 (1H, s), 8.16 (1H, d, J=8.5 Hz), 23.66 (1H, brs)

REFERENCE EXAMPLE 13

180 ml of 1N sodium hydroxide was added to 500 ml of a solution of 31.98 g of methyl N-(2-hydroxy- imino-4-methylpentanoyl)-(3',4',5'-trimethoxy)phenylalaninate in ethanol. The mixture was stirred at room temperature for 13 hours. The reaction mixture was subjected to distillation to remove ethanol. The residue was made acidic with hydrochloric acid and then extracted with ethyl acetate. The extract was washed with an aqueous solution saturated with sodium chloride, then dried with anhydrous magnesium sulfate, and subjected to distillation to remove the solvent to obtain 30.93 g of N-(2-hydroxyimino-4-methylpentanoyl)(3',4',5'-trimethoxy)phenylalanine.
White powder
$^1$H-NMR (CDCl$_3$, 250 MHz) δ ppm: 0.85 (3H, d, J=6.5 Hz), 0.8 (3H, d, J=6.5 Hz), 1.88–2.07 (1H, m), 2.48 (1H, dd, J=12.5 Hz, J=19.5 Hz), 2.50 (1H, dd, J=12.5 Hz, J=19.5 Hz), 3.05 (1H, dd, J=7.5 Hz, J=14 Hz), 3.20 (1H, dd, J=5 Hz, J=14 Hz), 3.77 (6H, s), 3.80 (3H, s), 4.92 (1H, dt, J=6 Hz, J=8.5 Hz), 6.38 (2H, s), 7.28 (1H, d, J=8.5 Hz)

REFERENCE EXAMPLE 14

The following compounds were obtained by using suitable starting materials and by employing the same manner as in Reference Example 13.
N-(2-Hydroxyimino-4-methylpentanoyl)-L-phenylalanine
White powder
Melting point: 120°–122° C.
N-(2-Hydroxyimino-4-methylpentanoyl)-o-benzyl-L-tyrosine
Colorless needle-like crystals
Melting point: 147°–148° C.
$N^{im}$-Benzyl-N-(2-hydroxyimino-4-methylpentanoyl)-L-histidine
White powder
$^1$H-NMR (DMSO-d$_6$, 250 MHz) δ ppm: 0.82 (6H, d, J=6.5 Hz), 1.80–2.00 (1H, m), 2.36 (2H, d, J=7.5 Hz), 2.94 (1H, dd, J=5 Hz, J=15 Hz), 3.03 (11H, dd, J=7 Hz, J=15 Hz), 4.56 (1H, dt, J=6 Hz, J=8 Hz), 5.19 (2H, s), 7.03 (1H, s), 7.20–7.30 (2H, m), 7.30–7.45 (3H, m), 7.95 (1H, s), 8.22 (1H, d, J=8 Hz), 11.81 (1H, s)

REFERENCE EXAMPLE 15

22.90 g of dicyclohexylcarbodiimide was added to 300 ml of a solution of 26.39 g of N-benzyloxyleucine and 13.35 g of N-hydroxysuccinimide in anhydrous dioxane. The mixture was stirred at room temperature for 2 hours. The reaction mixture was filtered to remove the insoluble materials, whereby a colorless solution was obtained. Separately, 20 ml of triethylamine was added to 300 ml of a suspension of 28.57 g of diethyl aminomalonate hydrochloride in anhydrous dioxane. To the mixture was applied an ultrasonic wave for 1 hour. Thereto was added the above colorless solution. The mixture was stirred at room temperature for 16 hours and then at a bath temperature of 100° C. for 3.5 hours. The reaction mixture was subjected to distillation to remove the solvent. The residue was dissolved in 1,000 ml of ethyl acetate. The solution was washed with 1N hydrochloric acid, an aqueous solution saturated with sodium hydrogen carbonate and an aqueous solution saturated with sodium chloride in this order, then dried with anhydrous magnesium sulfate, and subjected to distillation to remove the solvent to obtain 39.22 g of diethyl N-(N-benzyloxyleucyl)aminomalonate as a yellow oily substance.
$^1$H-NMR (CDCl$_3$, 250 MHz) δ ppm: 0.88 (3H, d, J=6.5 Hz), 0.91 (3H, d, J=6.5 Hz), 1.30 (6H, t, J=7 Hz), 1.35–1.55 (2H, m), 1.60–1.80 (1H, m), 3.57 (1H, dt, J=5.5 Hz, J=8.5 Hz), 4.20–4.40 (4H, m), 4.73, 4.82 (each 1H, d, J=12 Hz), 5.21 (1H, d, J=7 Hz), 5.69 (1H, d, J=5 Hz), 7.25–7.40 (5H, m), 7.52 (1H, d, J=7 Hz)

REFERENCE EXAMPLE 16

90 ml of 1N sodium hydroxide was added to 180 ml of a solution of 35.28 g of diethyl N-(N-benzyloxyleucyl)aminomalonate in ethanol, on ice-cooling. The mixture was diluted with 600 ml of water on ice-cooling and the resulting mixture was washed with diethyl ether (500 ml×2). The aqueous layer was adjusted to pH 1 with concentrated hydrochloric acid and extracted with ethyl acetate (500 ml×2)on ice-cooling. The extract was washed twice with an aqueous solution saturated with sodium chloride, then dried with anhydrous magnesium sulfate, and subjected to distillation to remove the solvent to obtain 28.72 g of ethyl N-(N-benzyloxyleucyl)aminomalonate as a white solid.
$^1$H-NMR (CDCl$_3$, 250 MHz) δ ppm: 0.89 (3H, d, J=6 Hz), 0.91 (3H, d, J=6 Hz), 1.32 (3H, t, J=7 Hz), 1.30–1.55 (2H, m), 1.55–1.80 (1H, m), 3.61 (1H, dd, J=6 Hz, J=8.5 Hz), 4.31 (2H, q, J=7 Hz), 4.77, 4.80 (each lit, d, J=12 Hz), 5.17 (0.5H, d, J=6.5 Hz), 5.19 (0.5H, d, J=5 Hz), 5.25 (2H, brs), 7.25–7.45 (5H, m), 7.71 (1H, d, J=6.5 Hz)

REFERENCE EXAMPLE 17

1.03 g of dicyclohexylcarbodiimide was added to 30 ml of a solution of 1.83 g of ethyl N-(N-benzyloxyleucyl)aminomalonate, 0.58 g of N-hydroxysuccinimide and 1.3 ml of (3-methoxybenzyl)amine in anhydrous dioxane. The mixture was stirred at room temperature for 2 hours. The reaction mixture was filtered to remove-the insoluble materials. The filtrate was diluted with 100 ml of ethyl acetate. The resulting solution was washed with 1N hydrochloric acid, an aqueous solution saturated with sodium hydrogen carbonate and an aqueous solution saturated with sodium chloride in this order, then dried with anhydrous magnesium sulfate, and subjected to distillation to remove the solvent. 1.49 g of the resulting yellow oily substance was purified by silica gel column chromatography (eluant: ethyl acetate/n-hexane=1/2)to obtain 0.96 g of ethyl N-(N-benzyloxyleucyl)-α-[N-(3-methoxybenzyl)carbamoyl]glycinate as a colorless oily substance.

¹H-NMR (CDCl₃, 250 MHz) δ ppm: 0.85 (1.5H, d, J=6.5 Hz), 0.87 (1.5H, d, J=6.5 Hz), 0.88 (1.5H, d, J=6.5 Hz), 0.90 (1.5H, d, J=6.5 Hz), 1.26 (1.5H, t, J=7 Hz), 1.27 (1.5H, t, J=7 Hz), 1.30–1.55 (2H, m), 1.55–1.75 (1H, m), 3.56 (1H, dt, J=6 Hz, J=8 Hz), 3.78 (3H, s), 4.15–4.35 (2H, m), 4.35–4.55 (2H, m), 4.70, 4.76 (each 0.5H, d, J=12 Hz), 4.72, 4.78 (each 0.5H, d, J=12 Hz), 5.13 (0.5H, d, J=7 Hz), 5.14 (0.5H, d, J=7 Hz), 6.75–7.00 (4H, m), 7.21 (1H, d, J=7.5 Hz), 7.30–7.50 (5H, m), 7.62 (0.5H, d, J=7 Hz), 7.75 (0.5H, d, J=7 Hz)

REFERENCE EXAMPLE 18

The following compounds were obtained by using suitable starting materials and by employing the same manner as in Reference Example 17.

Ethyl N-(N-benzyloxyleucyl)-α-[N-(2,4-dimethoxybenzyl)carbamoyl]glycinate

White solid

¹H-NMR (CDCl₃, 250 MHz) δ ppm: 0.85 (1.5H, d, J=6.5 Hz), 0.86 (1.5H, d, J=6.5 Hz), 0.88 (1.5H, d, J=6.5 Hz), 0.89 (1.5H, d, J=6.5 Hz), 1.21 (1.5H, t, J=7 Hz), 1.22 (1.5H, t, J=7 Hz), 1.30–1.55 (2H, m), 1.55–1.80 (1H, m), 3.54 (1H, dt, J=6 Hz, J=8 Hz), 3.79 (3H, s), 3.83 (3H, s), 4.20 (1H, q, J=7 Hz), 4.22 (1H, q, J=7 Hz), 4.38 (1H, d, J=6 Hz), 4.40 (1H, d, J=6 Hz), 4.70, 4.77 (each 0.5H, d, J=12 Hz), 4.71, 4.78 (each 0.5H, d, J=12 Hz), 5.04 (0.5H, d, J=7 Hz), 5.06 (0.5H, d, J=7 Hz), 6.41 (0.5H, dd, J=2.5 Hz, J=8 Hz), 6.42 (0.5H, dd, J=2.5 Hz, J=8 Hz), 6.45 (1H, d, J=2.5 Hz), 6.88 (1H, brt, J=8 Hz), 7.14 (1H, d, J=8 Hz), 7.25–7.45 (5H, m), 7.59 (0.5H, d, J=7 Hz), 7.72 (0.5H, d, J=7 Hz)

Ethyl N-(N-benzyloxyleucyl)-α-[N-(3,5-di-tert-butyl-4hydroxybenzyl)carbamoyl]glycinate Brown oily substance ¹H-NMR (CDCl₃, 250 MHz) δ ppm: 0.87 (3H, d, J=6.5 Hz), 0.89 (3H, d, J=6.5 Hz), 1.23 (2H, J=7 Hz), 1.20–1.55 (2H, m), 1.42 (18H, s), 1.55–1.75 (1H, m), 3.40–3.65 (1H, m), 4.20–4.50 (4H, m), 4.65–4.80 (2H, m), 5.09 (0.5H, d, J=7 Hz), 5.10 (0.5H, d, J=7 Hz), 5.20 (1H, s), 5.62–5.78 (1H, br), 6.63 (1H, brt, J=5 Hz), 7.05 (2H, s), 7.30–7.45 (5H, m), 7.58 (0.5H, d, J=7 Hz), 7.78 (0.5H, d, J=7 Hz)

Ethyl N-(N-benzyloxyleucyl)-α-[4-(2-methoxyphenyl)-1-piperazinylcarbonyl]glycinate Colorless oily substance ¹H-NMR (CDCl₃, 250 MHz) δ ppm: 0.87 (3H, d, J=7 Hz), 0.90 (3H, d, J=7 Hz), 1.27 (3H, t, J=7 Hz), 1.30–1.55 (2H, m), 1.55–1.80 (1H, m), 3.00–3.25 (4H, m), 3.45–3.65 (1H, m), 3.75–4.10 (4H, m), 3.89 (3H, s), 4.23 (2H, q, J=7 Hz), 4.77 (0.8H, dd, J=12 Hz, J=19.5 Hz), 4.78 (1.2H, dd, J=12 Hz, J=19.5 Hz), 5.66 (1H, d, J=7.5 Hz), 5.71 (0.4H, d, J=5 Hz), 5.78 (0.6H, d, J=6.5 Hz), 6.85–7.15 (4H, m), 7.30–7.50 (5H, m), 7.66 (0.6H, d, J=7.5 Hz), 7.81 (0.4H, d, J=7.5 Hz)

REFERENCE EXAMPLE 19

2.5 ml of 1N sodium hydroxide was added to 20 ml of a solution of 0.96 g of ethyl N-(N-benzyl- oxyleucyl)-α-[N-3-methoxybenzyl)carbamoyl]glycinate in ethanol, with ice-cooling. The mixture was stirred at room temperature for 4 hours. The reaction mixture was diluted with 70 ml of water. The resulting solution was adjusted to pH 1 with concentrated hydrochloric acid and extracted with ethyl acetate. The extract was washed twice with an aqueous solution saturated with sodium chloride, then dried with anhydrous magnesium sulfate, and subjected to distillation to remove the solvent to obtain 1.03 g of N-(N-benzyloxyleucyl)-α-[N-(3-methoxybenzyl)carbamoyl]glycine as a white solid.

¹H-NMR (CDCl₃, 250 MHz) δ ppm: 0.84 (3H, d, J=6.5 Hz), 0.89 (3H, d, J=6.5 Hz), 1.25–1.50 (2H, m), 1.50–1.70 (1H, m), 3.50–3.70 (1H, m), 3.78 (3H, s), 4.10–4.22 (0.8 H, m), 4.35 (1.2H, dd, J=6 Hz, J=12 Hz), 4.56 (0.8H, s), 4.60 (1.2H, s), 5.08–5.13 (0.4H, m), 5.14–5.23 (0.6H, m), 6.70–6.90 (2H, m), 7.15–7.40 (6H, m), 7.63 (1H, brd, J=6 Hz)

REFERENCE EXAMPLE 20

The following compounds were obtained by using suitable starting materials and by employing the same manner as in Reference Example 19.

N-(N-Benzyloxyleucyl)-2-[N-(2,4-dimethoxybenzyl)carbamoyl]glycine

Light yellow oily substance

¹H-NMR (CDCl₃, 250 MHz) δ ppm: 0.80–0.95 (6H, m), 1.25–1.50 (2H, m), 1.50–1.75 (1H, m), 3.52 (0.5H, d, J=8 Hz), 3.63 (0.5H, dd, J=6 Hz, J=8.5 Hz), 3.76 (1.5H, s), 3.77 (1.5H, s), 3.78 (1.5H, s), 3.79 s), 4.31 (1H, d, J=5.5 Hz), 4.35 (1H, d, J=5.5 Hz), 4.57, 4.63 (each 1H, d, J=12.5 Hz), 5.02 (0.5H, d, J=6.5 Hz), 5.10 (0.5H, d, J=6.5 Hz), 5.10–6.20 (1H, br), 6.41 (1H, dd, J=1.5 Hz, J=8 Hz), 6.42 (1H, d, J=1.5 Hz), 7.10 (0.5H, d, J=8 Hz), 7.12 (0.5H, d, J=8 Hz), 7.20–7.40 (5.5H, m), 7.52 (0.5H, d, N-(N-benzyloxyleucyl)-α-[N-(3,5-di-tert-butyl-4-hydroxybenzyl)carbamoyl]glycine Brown oily substance ¹H-NMR (CDCl₃, 250 MHz) δ ppm: 0.80–0.95 (6H, m), 1.30–1.50 (2H, m), 1.41 (18H, s), 1.55–1.70 (1H, m), 3.90–4.05 (1H, m), 4.25–4.40 (2H, m), 4.45–4.60 (2H, m), 5.08 (0.5H, d, J=6.5 Hz), 5.13 (0.5H, d, J=6.5 Hz), 5.20 (1H, brs), 6.61 (0.5H, brt, J=6.5 Hz), 6.95–7.10 (2H, m), 7.14 (0.5H, brt, J=6.5 Hz), 7.20–7.40 (5H, m), 7.71 (1H, brd, J=8.5 Hz)

N-(N-Benzyloxyleucyl)-α-[4-(2-methoxyphenyl)---piperazinylcarbonyl]glycine

Yellow oily substance

¹H-NMR (CDCl₃, 250 MHz) δ ppm: 0.85 (3H, d, J=6.5 Hz), 0.88 (3H, d, J=6.5 Hz), 1.35–1.55 (2H, m), 1.55=1.75 (1H, m), 2.95–3.25 (4H, m), 3.60 (1H, dd, J=5.5 Hz, J=8.5 Hz), 3.75–3.90 (4H, m), 3.86 (3H, s), 4.71 (1H, dd, J=2.5 Hz, J=2 Hz), 4.78 (1H, dd, J=3.5 Hz, J=12 Hz), 5.59 (0.5H, d, J=7.5 Hz), 5.63 (0.5H, d, J=12 Hz), 5.59 (0.5H, d, J=7.5 Hz), 5.63 (0.5H, d, J=7.5 Hz), 5.69 (2H, brs), 6.85–6.95 (3H, m), 6.95–7.10 (1H, m), 7.25–7.45 (5H, m), 8.00 (0.8 H, d, J=7.5 Hz), 8.06 (0.5H, d, J=7.5 Hz)

REFERENCE EXAMPLE 21

8.68 g of dicyclohexylcarbodiimide was added to 200 ml of a solution of 8.73 g of 3-(3-indolyl)-2-hydroxyiminopropionic acid and 4.83 g of N-hydroxysuccinimide in anhydrous dioxane, with ice-cooling. The mixture was stirred at room temperature for 2 hours. The reaction mixture was filtered to remove the insoluble materials, to obtain a brown solution. Separately, 5.6 ml of triethylamine was added to 70 ml of a suspension of 7.27 g of methyl L-leucinate hydrochloride in anhydrous dioxane. The mixture was stirred at room temperature for 2 hours. Thereto was added the above brown solution. The mixture was stirred for 16 hours. The reaction mixture was diluted with 700 ml of ethyl acetate. The resulting solution was washed with 1N hydrochloric acid, an aqueous solution saturated with sodium chloride and an aqueous solution saturated with sodium hydrogen carbonate in this order, then dried with anhydrous magnesium sulfate, and subjected to distillation to remove the solvent, to obtain 13.81 g of methyl N-[2-hydroxyimino-3-(3-indolyl)propionyl]-L-leucinate as a brown oily substance.

$^1$H-NMR (CDCl$_3$, 250 MHz) δ ppm: 0.87 (3H, d, J=6 Hz), 0.89 (3H, d, J=6 Hz), 1.45–1.75 (3H, m), 3.70 (3H, s), 4.08 (2H, s), 4.65 (1H, dt, J=5.5 Hz, J=8.5 Hz), 6.96 (1H, d, J=2.5 Hz), 7.09 (1H, d, J=7 Hz), 7.15 (1H, d, J=7 Hz), 7.26 (1H, d, J=7 Hz), 7.28 (1H, d, J=7 Hz), 7.78 (1H, d, J=7 Hz), 7.93 (1H, brs), 9.29 (1H, s)

REFERENCE EXAMPLE 22

The following compounds were obtained by using suitable starting materials and by employing the same manner as in Reference Example 21.

Methyl N-[2-hydroxyimino-3-(3-indolyl)propionyl]-L-phenylalaninate

Brown oily substance $^1$H-NMR (CDCl$_3$, 250 MHz) δ ppm: 3.01 (1H, dd, J=6 Hz, J=14 Hz), 3.09 (1H, dd, J=6 Hz, J=14 Hz), 3.65 (3H, s), 4.04, 4.11 (each 1H, d, J=14 Hz), 4.87 (1H, dt, J=6 Hz, J=8 Hz), 6.85–7.00 (2H, m), 7.04 (1H, d, J=2.5 Hz), 7.05–7.25 (6H, m), 7.30 (1H, d, J=7.5 Hz), 7.78 d, J=7.5 Hz), 8.00 (1H, brs), 8.56 (1H, brs)

Methyl N-[2-hydroxyimino-3-(3-indolyl)propionyl]-L-methioninate

Brown oily substance $^1$H-NMR (CDCl$_3$, 250 MHz) δ ppm: 1.75–2.05 (1H, m), 1.98 (3H, s), 2.05–2.20 (1H, m), 2.40 (2H, t, J=7 Hz), 3.70 (3H, s), 4.08 (2H, s), 4.74 (1H, dt, J=5.5 Hz, 8 Hz), 7.02 (1H, d, J=2.5 Hz), 7.08 (1H, t, J=8 Hz), 7.15 (1H, t, J=8 Hz), 7.26 (1H, d, J=8 Hz), 7.37 (1H, d, J=8 Hz), 7.78 (1H, d, J=8 Hz), 8.03 (1H, brs), 9.24 (1H, brs)

Methyl O-benzyl-N-[2-hydroxyimino-3-(3-indolyl)-propionyl]-L-serinate

Light yellow foam-like substance $^1$H-NMR (CDCl$_3$, 250 MHz) δ ppm: 3.60 (1H, dd, J=3.5 Hz, J=9.5 Hz), 3.68 (3H, 3.60 (1H, dd, J=3.5 Hz, J=9.5 Hz), 4.06 (2H, brs), 4.36, 4.45 (each 1H, d, J=12 Hz), 4.76 (1H, dt, J=3.5 Hz, 8.5 Hz), 6.99 (1H, s), 7.05

7.35 (7H, m), 7.63 (1H, d, J=8 Hz), 7.78 d, J=7.5 Hz), 7.90 (1H, brs), 8.89 (1H, brs)

Diethyl N-[2-hydroxyimino-3-(3-indolyl)propionyl]aminomalonate

Brown oily substance $^1$H-NMR (CDCl$_3$, 250 MHz) δ ppm: 1.24 (6H, t, J=7 Hz), 4.04 (2H, s), 4.10–4.35 (4H, m), 5.18 (1H, d, J=7 Hz), 6.98 (1H, d, J=2.5 Hz), 7.08 (1H, t, J=7 Hz), 7.14 (1H, t, J=7 Hz), 7.24 (1H, d, J=7 Hz), 7.77 (1H, d, J=7 Hz), 7.79 (1H, d, J=7 Hz), 8.05 (1H, brs), 9.30 (1H, brs)

Diethyl N-[2-hydroxyimino-3-(3-indolyl)propionyl]-L-aspartate

Brown oily substance $^1$H-NMR (CDCl$_3$, 250 MHz) δ ppm: 1.19 (3H, t, J=7 Hz), 1.20 (3H, t, J=7 Hz), 2.80 (1H, dd, J=5 Hz, J=17 Hz), 2.99 (1H, dd, J=5 Hz, J=17 Hz), 4.07 (2H, s), 4.17 (2H, q, J=7 Hz), 4.18 (2H, q, J=7 Hz), 4.87 (1H, dt, J=5 Hz, J=8.5 Hz), 7.07 (1H, d, J=2.5 Hz), 7.12 (1H, t, J=7.5 Hz), 7.15 (1H, t, J=7 Hz), 7.28 (1H, d, J=7 Hz), 7.67 (1H, d, J=8.5 Hz), 7.79 (1H, d, J=7.5 Hz), 8.03 (1H, brs), 8.58 (1H, s)

Methyl O-benzyl-N-[2-hydroxyimino-3-(3-indolyl)propionyl]-L-tyrosinate

Brown oily substance $^1$H-NMR (CDCl$_3$, 250 MHz) δ ppm: 2.92 (1H, dd, J=6 Hz, J=14 Hz), 3.02 (1H, dd, J=6 Hz, J=14 Hz), 3.62 (3H, s), 4.10, 4.13 (each 1H, s), 4.81 (1H, dd, J=6 Hz, J=14 Hz), 4.88 (2H, s), 6.66, 6.78 (each 2H, d, J=8.5 Hz), 6.96 (1H, d, J=2 Hz), 7.09 (1H, t, J=7.5 Hz), 7.15 (1H, t, J=7.5 Hz), 7.24 (1H, d, J=7 Hz), 7.25–7.45 (5H, m), 7.78 (1H, d, J=7 Hz), 8.06 (1H, brs)

Methyl N-[2-hydroxyimino-3-(3-indolyl)propionyl]-L-prolinate

Brown oily substance $^1$H-NMR (CDCl$_3$, 250 MHz) δ ppm: 1.30–1.55 (0.5H, m), 1.55–1.95 (3H, m), 1.95–2.10 (0.5H, m), 3.20–3.45 (2H, m), 3.67 (3H, s), 4.00, 4.13 (each 0.7H, d, J=14.5 Hz), 4.18, 4.23 (each 0.3H, d, J=8 Hz), 4.40 (0.7H, dd, J=5.5 Hz, 8.5 Hz), 4.49 (0.3H, brd, J=4.5 Hz), 7.00–7.20 (3H, m), 7.20–7.40 (1H, m), 7.70 (1H, d, J=7 Hz), 8.43 (1H, brs), 9.47 (1H, s)

REFERENCE EXAMPLE 23

1.24 g of dicyclohexylcarbodiimide was added to 30 ml Of a solution of 1.77 g of N-benzyloxy-DL-tryptophane and 0.70 g of N-hydroxysuccinimide in anhydrous dioxane, with ice-cooling. The mixture was stirred at room temperature for 2 hours. The reaction mixture was filtered to remove the insoluble materials, whereby a light brown solution was obtained. Separately, 0.8 ml of triethylamine was added to 20 ml of a suspension of 0.89 g of methyl L-serinate hydrochloride in anhydrous dioxane. The mixture was stirred at room temperature for 2 hours. Thereto was added the above light brown solution. The resulting mixture was stirred at room temperature for 66 hours. The reaction mixture was diluted with 200 ml of ethyl acetate. The resulting solution was washed with 1N hydrochloric acid and an aqueous solution saturated with sodium chloride, then dried with anhydrous magnesium sulfate, and subjected to distillation to remove the solvent, to obtain 2.07 g of methyl (N-benzyloxy-DL-tryptophyl)-L-serinate as a brown oily substance.

$^1$H-NMR (DMSO-d$_6$, 250 MHz) δ ppm: 2.70–2.87 (1H, m), 2.97 (1H, dd, J=6 Hz, J=14.5 Hz), 3.45–3.80 (2H, m), 3.60, 3.61 (each 1.5H, s), 3.80–3.95 (1H, m), 4.30–4.55 (1H, m), 4.62 (2H, s), 5.08 (1H, dd, J=5.5 Hz, J=10.5 Hz), 6.49 (1H, d, J=7 Hz), 6.96 (1H, t, J=7.5 Hz), 7.06 (1H, t, J=7.5 Hz), 7.13 (1H, s), 7.27 (5H, s), 7.32 (1H, d, J=7.5 Hz), 7.51 (1H, d, J=7.5 Hz), 8.15, 8.22 (each 0.5H, d, J=8 Hz), 10.83 (1H, brs)

EXAMPLE 1

1.09 g of dicyclohexylcarbodiimide was added to 25 ml of a solution of 2.17 g of (3RS,6SR)-3-benzyl-1-benzyloxy-3-carboxy-6-isobutylpiperazine-2,5-dione and 0.63 g of N-hydroxysuccinimide in anhydrous dioxane. The mixture was stirred at room temperature for 2 hours. Thereto was added 0.80 g of 2-aminobenzothiazole. The mixture was stirred at room temperature for 23 hours. The reaction mixture was diluted with 200 ml of ethyl acetate. The resulting solution was washed with an aqueous solution saturated with sodium hydrogen carbonate and an aqueous solution saturated with sodium chloride, then dried with anhydrous magnesium sulfate, and subjected to distillation to remove the solvent. The residue was crystallized using ethyl acetate, to obtain 2.77 g of (3RS,6SR)-3-(benzothiazol-2-yl)-carbamoyl-3-benzyl-1-benzyloxy-6-isobutylpiperazine-2,5-dione as a white solid.

$^1$H-NMR (CDCl$_3$, 250 MHz) δ ppm: 0.75 (3H, d, J=6 Hz), 0.76 (3H, d, J=6 Hz), 1.50–1.85 (3H, m), 3.26, 3.64 (each 1H, d, J=13.5 Hz), 3.51 (1H, t, J=6 Hz), 4.49, 4.81 (each 1H, d, J=10 Hz), 6.95 (1H, brs), 7.10–7.20 (2H, m), 7.25–7.40 (9H, m), 7.48 (1H, t, J=8 Hz), 7.85 (2H, t, J=8 Hz)

The compounds of Examples 27–29 and 31–39 described later were obtained by using suitable starting materials and by employing the same manner as in Example 1.

EXAMPLE 2

0.80 g of 10% palladium-carbon was added to 30 ml of a solution of 1.56 g of (3RS,6SR)-3-(benzothiazol-2-yl)carbamoyl-3-benzyl-1-benzyloxy-6-isobutylpipera- zine-2,5-dione in dioxane. The mixture was stirred at room temperature for 4 hours in a hydrogen current. The reaction mixture was filtered to remove the catalyst. The filtrate was subjected to distillation to remove the solvent. The resulting light brown oily substance was recrystallized using dichloromethane, to obtain 0.56 g of (3RS,6SR)-3-(benzothiazol-2-yl)carbamoyl-3-benzyl-1-hydroxy-6-isobutylpiperazine-2,5-dione.

White solid
Melting point: 222–225° C. (decomp.)

The compounds of Examples 9–26, 28–29, 33, 37–39, 47–62 and 64–65 described later were obtained by using suitable starting materials and by employing the same manner as in Example 2.

EXAMPLE 3

In 20 ml of 1N hydrochloric acid (an ethanolic solution)was dissolved 3.32 g of (3RS,6SR)-1-(2-tetrahydropyranyloxy)-6-isobutyl-3-[N-(3-methoxybenzyl)carbamoyl-3-methylpiperazine-2,5-dione. The solution was stirred for 5 minutes and then subjected to distillation to remove the solvent. To the residue was added 30 ml of a 1N aqueous sodium hydroxide solution. The mixture was washed with dichloromethane (30 ml×2) and diethyl ether (30 ml). The aqueous layer was adjusted to pH 2–3 with concentrated hydrochloric acid and extracted with ethyl acetate (30 ml×2). The extract was dried with anhydrous magnesium sulfate and then subjected to distillation to remove the solvent. The residue was recrystallized from diethyl ether to obtain 1.26 g of (3RS,6SR)-1-hydroxy-6-isobutyl-3-[N-(3-methoxybenzyl)]carbamoyl-3-methylpiperazine-2,5-dione.
Light brown solid Melting point: 151.5–153.5° C.

EXAMPLE 4

13.21 g of dicyclohexylcarbodiimide was added to 500 ml of a solution of 32.83 g of N-(N-benzyloxyleucyl)-(3',5'-di-tert-butyl)tyrosine and 7.71 g of N-hydroxysuccinimide in anhydrous dioxane. The mixture was stirred at room temperature for 3 days and then kept at 120° C. for 1.5 hours. The reaction mixture was allowed to cool. The resulting insoluble materials were removed by filtration, and the filtrate was concentrated to 200 ml under reduced pressure. The concentrate was diluted With 1,000 ml of ethyl acetate. The resulting solution was washed with 1N hydrochloric acid, an aqueous solution saturated with sodium hydrogen carbonate and an aqueous solution saturated with sodium chloride, then dried with anhydrous magnesium sulfate, and subjected to vacuum distillation to remove the solvent. The residue was purified by silica gel column chromatography (eluant: ethyl acetate/n-hexane=1/2)to obtain 11.54 g of a compound (A) and 5.42 g of a compound (B).
Compound (A)
(3RS,6RS)-1-Benzyloxy-3-(3,5-di-tert-butyl-4-hydroxybenzyl)-6-isobutylpiperazine-2,5-dione
Melting point: 198.5°–200.5° C. (decomp.) (recrystallized from ethyl acetate)

Colorless needle-like crystals
Compound (B)
(3RS, 6SR)-1-Benzyloxy-3-(3,5-di-tert-butyl-4-hydroxybenzyl)-6-isobutylpiperazine-2,5-dione
Light yellow solid
$^1$H-NMR (CDCl$_3$, 250 MHz) δ ppm: 0.86 (3H, d, J=6 Hz), 0.88 (3H, d, J=6 Hz), 1.43 (18H, s), 1.60–1.95 (3H, m), 2.74 (1H, dd, J=9.5 Hz, J=14 Hz), 3.44 (1H, dd, J=3.5 Hz, J=14 Hz), 3.77 (1H, t, J=6 Hz), 4.15 (1H, dd, J=3.5 Hz, J=9.5 Hz), 4.82, 4.97 (each 1H, d, J=10.5 Hz), 5.21 (1H, s), 5.67 (1H, brs), 7.01 (2H, s), 7.37 (5H, s)

EXAMPLE 5

0.41 g of dicyclohexylcarbodiimide was added to 20 ml of a solution of 0.91 g of N-(N-benzyloxyleucyl)-α-[N-(3-methoxybenzyl)]carbamoylglycine and 0.23 g of N-hydroxysuccinimide in anhydrous dioxane. The mixture was stirred at room temperature for 16 hours. The reaction mixture was filtered to remove the insoluble materials. The filtrate was diluted with 50 ml of ethyl acetate. The resulting solution was washed with 1N hydrochloric acid and an aqueous solution saturated with sodium hydrogen carbonate, then dried with anhydrous magnesium sulfate, and subjected to distillation to remove the solvent, to obtain 0.81 g of 1-benzyloxy-6-isobutyl-3-[N-(3-methoxybenzyl)]carbamoylpiperazine-2,5-dione as a mixture of a cis form and a trans form.

Light brown solid
$^1$H-NMR (CDCl$_3$, 250 MHz) δ ppm: 0.85 (1.5H, d, J=6.5 Hz), 0.86 (1.5H, d, J=6.5 Hz), 0.92 (3H, d, J=6 Hz), 1.60–2.00 (3H, m), 3.78 (1.5H, s), 3.80 (1.5H, s), 4.00 (1H, t, J=6 Hz), 4.43 (1H, d, J=6 Hz), 4.46 (0.5H, d, J=6 Hz), 4.53 (0.5 H, d, J=6 Hz), 4.54 (0.5H, s-like), 4.62 (0.5H, d, J=2.5 Hz), 4.88, 4.99 (each 0.5H, d, J=10.5 Hz), 4.95, 5.01 (each 0.5H, d, J=10.5 Hz), 6.46 (0.5H, brs), 6.90 (0.5H, brs), 6.70–7.00 (3H, m), 7.15–7.28 (1H, m), 7.37 (2.5H, s), 7.15–7.28 (1H, m), 7.37 (2.5H, s), 7.40 (2.5H, s), 7.54 (0.5H, brt, J=6 Hz), 8.53 (0.5H, brt, J=6 Hz)

EXAMPLE 6

7.00 g of N,N-carbonyldiimidazole was added to 200 ml of a solution of 17.40 g of N-(N-benzyloxyleucyl)-(2',4'-dimethoxy)phenylalanine in anhydrous dioxane. The mixture was stirred at room temperature for 16 hours. The reaction mixture was diluted with 1,000 ml of ethyl acetate. The resulting solution was washed with 10% citric acid, a 10% aqueous sodium hydrogen carbonate solution and an aqueous solution saturated with sodium chloride in this order, then dried with anhydrous magnesium sulfate, and subjected to vacuum distillation to remove the solvent. The resulting yellow oily substance was subjected to silica gel column chromatography (eluant: ethyl acetate/n-hexane=1/1 - 3/1) to obtain 3.79 g of a yellow vitreous compound (C)and 1.53 g of a light yellow solid compound (D).
Compound (C)
(3RS,6RS)-1-Benzyloxy-3-(2,4-dimethoxybenzyl)-6-isobutylpiperazine-2,5-dione
$^1$H-NMR (CDCl$_3$, 250 MHz) δ ppm: 0.84 (6H, d, J=6.5 Hz), 1.15–1.35 (1H, m), 1.40–1.55 (1H, m), 1.75–1.95 (1H, m), 2.92 (1H, dd, J=8 Hz, 13.5 Hz), 3.36 (1H dd, J=4.5 Hz, 13.5 Hz), 3.78 (3H, s), 3.80 (3H, s), 3.88 (1H, dd, J=5.5 Hz, 8 Hz), 4.20–4.35 (1H, m), 4.94, 5.02 (each 1H, d, J=10.5 Hz), 5.65 (1H, brs), 6.41 (1H, dd, J=2.5 Hz, J=8 Hz), 6.45 (1H, d, J=2.5 Hz), 7.04 (1H, d, J=8 Hz), 7.30–7.50 (5H, m)

Compound (D)

(3RS,6SR)-1-Benzyloxy-3-(2,4-dimethoxybenzyl)-6-isobutylpiperazine-2,5dione $^1$H-NMR (CDCl$_3$, 250 MHz) δ ppm: 0.86 (3H, d, J=6.5 Hz), 0.87 (3H, d, J=6.5 Hz), 1.50–1.90 (3H, m), 2.93 (1H, dd, J=7.5 Hz, J=14 Hz), 3.51 (1H, dd, J=4 Hz, J=14 Hz), 3.75 (1H, t, J=6 Hz), 3.80 (3H, s), 3.85 (3H, s), 4.23 (1H, dd, J=4 Hz, 7.5 Hz), 4.82, 4.97 (each 1H, d, J=11 Hz), 6.00 (1H, brs), 76.47 (1H, dd, J=2.5 Hz, J=8 Hz), 6.50 (1H, d, J=2.5 Hz), 7.15 (1H, d, J=8 Hz), 7.25–7.40 (5H, m)

EXAMPLE 7

150 ml of 7N hydrochloric acid. (an ethanolic solution) was dropwise added, in 20 minutes at room temperature, to 150 ml of a solution of 8.77 g of N-(2-hydroxyimino-4-methylpentanoyl)-L-phenylalanine and 3.28 g of borane-trimethylamine in ethanol. The mixture was stirred for 24 hours. The reaction mixture was subjected to vacuum distillation at room temperature to remove the solvent. The residue was dissolved in dichloromethane. The solution was washed with an aqueous solution saturated with sodium chloride and an aqueous solution saturated with sodium hydrogen carbonate, then dried with anhydrous magnesium sulfate, and subjected to distillation to remove the solvent. To the residue was added 100 ml of toluene. The mixture was refluxed for 1 hour and then subjected to distillation to remove the solvent. The resulting brown oily substance was subjected to silica gel column chromatography (eluant: dichloromethane/methanol=15/1) to obtain 1.77 g of a compound (E) and 1.65 g of a compound (F).

Compound (E)

(3S, 6s)-3-benzyl-1-hydroxy-6-isobutylpiperazine-2,5-dione

Light orange prismatic crystals

Melting point: 152°–153° C. (recrystallized from dichloromethane)

Compound (F)

(3S,6R)-3-Benzyl-1-hydroxy-6-isobutylpiperazine-2,5-dione

Light brown needle-like crystals

Melting point: 203°–204° C. (recrystallized from chloroformdiethyl ether)

EXAMPLE 8

200 ml of 7N hydrochloric acid (an ethanolic solution) was added to 200 ml of a solution of 13.81 g of methyl N-[2-hydroxyimino-3-(3-indolyl)propionyl]-L-leucinate and 4.51 g of borane-trimethylamine in ethanol, with ice-cooling. The mixture was stirred at room temperature for 16 hours. The reaction mixture was subjected to distillation to remove the solvent. The residue was mixed with 150 ml of dichloromethane and 150 ml of an aqueous solution saturated with sodium hydrogen carbonate to conduct distribution. The organic layer was dried with anhydrous magnesium sulfate and then subjected to distillation to remove the solvent. The residue was made into a toluene solution (100 ml). The solution was refluxed for 1 hour and then subjected to distillation to remove the solvent. 15.64 g of the resulting brown oily substance was purified by silica gel column chromatography (eluant: dichloromethane/methanol=50/1 –15/1) to obtain 1.28 g of a compound (G) of cis form and 1.30 g of a compound (H) of trans form.

Compound (G)

(3S,6S)-1-Hydroxy-6-(3-indolylmethyl)-3-isobutylpiperazine-2,5-dione

Light orange solid

Melting point: 146°–148° C. (decomp.) (recrystallized from chloroform-n-hexane)

Compound (H)

(3S, 6R)-1-Hydroxy-6-(3-indolylmethyl)-3-isobutylpiperazine-2,5-dione

Light orange solid

Melting point: 128°–129.5° C. (decomp.)

By using suitable starting materials and by employing the same manners as in Examples 4, 5, 6 and 7, there were obtained the compounds of Examples 9–45 shown in the following Tables 1–13.

TABLE 1

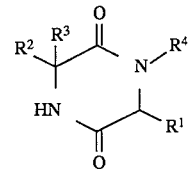

Example 9

Structures of substituents

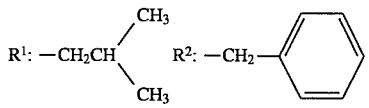

R$^3$: H  R$^4$: —OH
Configuration:  3S, 6S
Crystal form: light orange prisms (recrystallized from dichloromethane)
Melting point: 152–153° C.
Salt form: free Example 10

Structures of substituents

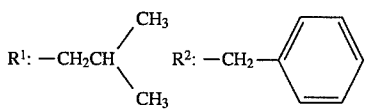

R$^3$: H  R$^4$: —OH
Configuration:  3S, 6R
Crystal form: light brown needles (recrystallized from chloroform-diethyl ether)
Melting point: 203–204° C.
Salt form: free

TABLE 2

Example 11

Structures of substituents

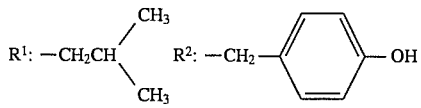

R$^3$: H  R$^4$: —OH
Configuration:  3S, 6R
Crystal form: colorless needles (recrystallized from ethanol)
Melting point: 243–245° C.
Salt form: free

TABLE 2-continued

Example 12

Structures of substituents

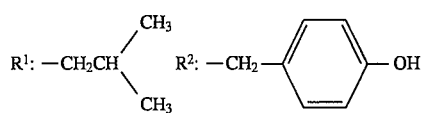

| | |
|---|---|
| R³: H | R⁴: —OH |
| Configuration: | 3S, 6R |
| Crystal form: | colorless needles (recrystallized from chloroform) |
| Melting point: | 155–158° C. |
| Salt form: | free |

Example 13

Structures of substituents

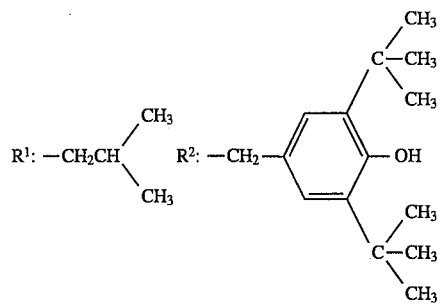

| | |
|---|---|
| R³: H | R⁴: —OH |
| Configuration: | 3RS, 6RS |
| Crystal form: | colorless needles (recrystallized from ethyl acetate) |
| Melting point: | 219–221° C. |
| Salt form: | free |

TABLE 3

Example 14

Structures of substituents

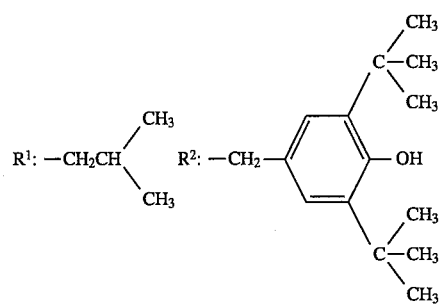

| | |
|---|---|
| R³: H | R⁴: —OH |
| Configuration: | 3RS, 6SR |
| Crystal form: | colorless columns (recrystallized from ethyl acetate) |
| Melting point: | 182–185° C. |
| Salt form: | free |

Example 15

Structures of substituents

TABLE 3-continued

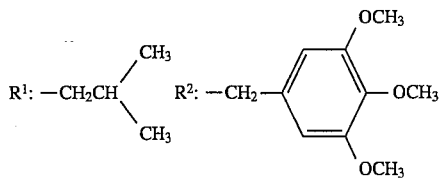

| | |
|---|---|
| R³: H | R⁴: —OH |
| Configuration: | 3RS, 6RS |
| Crystal form: | light orange solid |
| Melting point: | 154–155.5° C. |
| Salt form: | free |

Example 16

Structures of substituents

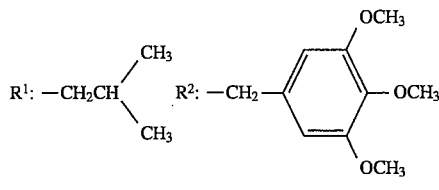

| | |
|---|---|
| R³: H | R⁴: —OH |
| Configuration: | 3RS, 6SR |
| Crystal form: | white solid |
| Melting point: | 141.5–142.5° C. |
| Salt form: | free |

TABLE 4

Example 17

Structures of substituents

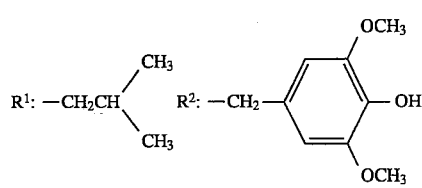

| | |
|---|---|
| R³: H | R⁴: —OH |
| Configuration: | 3RS, 6RS |
| Crystal form: | colorless prisms (recrystallized from methanol-chloroform) |
| Melting point: | 216–216.5° C. |
| Salt form: | free |

Example 18

Structures of substituents

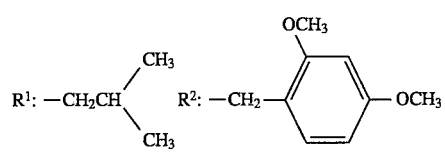

| | |
|---|---|
| R³: H | R⁴: —OH |
| Configuration: | 3RS, 6RS |
| Crystal form: | colorless prisms (recrystallized from isopropyl alcohol-diisopropyl ether) |
| Melting point: | 117.5–119° C. |
| Salt form: | free |

Example 19

Structures of substituents

TABLE 4-continued

R¹: —CH₂CH(CH₃)₂     R²: —CH₂—(3-OCH₃, 4-OCH₃-phenyl)

R³: H                    R⁴: —OH
Configuration:           3RS, 6SR
Crystal form:            light orange prisms (recrystallized from isopropyl alcohol-diisopropyl ether)
Melting point:           125–126.5° C.
Salt form:               free

TABLE 5

Example 20

Structures of substituents

R¹: —CH₂CH(CH₃)₂     R²: —CH₂—(2,6-dichloro-4-OH-phenyl)

R³: H                    R⁴: —OH
Configuration:           3S, 6S
Crystal form:            colorless needles (recrystallized from methanol)
Melting point:           234.5–241° C.
Salt form:               free

Example 21

Structures of substituents

R¹: —CH₂CH(CH₃)₂     R²: —CH₂—(2,6-dichloro-4-OH-phenyl)

R³: H                    R⁴: —OH
Configuration:           3S, 6R
Crystal form:            colorless needles (recrystallized from dichloromethane-methanol)
Melting point:           218–220.5° C.
Salt form:               free

Example 22

Structures of substituents

R¹: —CH₂CH(CH₃)₂     R²: —CH₂—(2,6-dimethyl-4-OH-phenyl)

R³: H                    R⁴: —OH
Configuration:           3RS, 6RS
Crystal form:            colorless needles (recrystallized from ethyl acetate)
Melting point:           187–188.5° C.
Salt form:               free

TABLE 6

Example 23

Structures of substituents

R¹: —CH₂CH(CH₃)₂     R²: —CH₂—(4-OCH₂-phenyl-phenyl)

R³: H                    R⁴: —OH
Configuration:           3S, 6S
Crystal form:            light brown solid
Salt form:               free

Example 24

Structures of substituents

R¹: —CH₂CH(CH₃)₂     R²: —CH₂—(4-OCH₂-phenyl-phenyl)

R³: H                    R⁴: —OH
Configuration:           3S, 6R
Crystal form:            light brown solid
Salt form:               free

Example 25

Structures of substituents

R¹: —CH₂CH(CH₃)₂     R²: —CH₂—(1-benzyl-imidazol-4-yl)

R³: H                    R⁴: —OH
Configuration:           3S, 6S
Crystal form:            white solid
Salt form:               free

TABLE 7

Example 26

Structures of substituents

R¹: —CH₂CH(CH₃)₂     R²: —CH₂—(1-benzyl-imidazol-4-yl)

R³: H   R⁴: —OH
Configuration: 3S, 6R
Crystal form: colorless needles (recrystallized from methanol)
Melting point: 185.5–186.5° C.
Salt form: free

Example 27

Structures of substituents

TABLE 7-continued

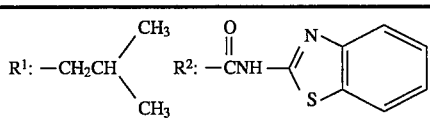

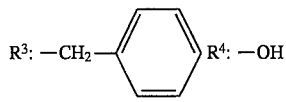

Configuration: 3RS, 6SR
Crystal form: white solid
Melting point: 222–225° C. (decompd.)
Salt form: free Example 28

Structures of substituents

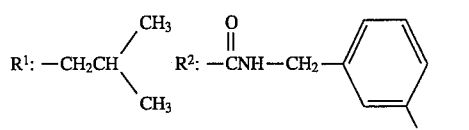

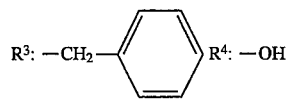

Configuration: 3RS, 6SR
Crystal form: white solid
Melting point: 145–147.5° C.
Salt form: free

TABLE 8

Example 29

Structures of substituents

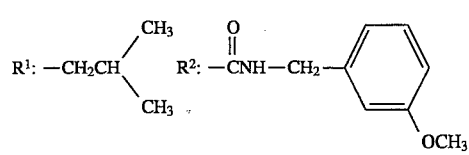

$R^3$: —$CH_3$  $R^4$: —OH
Configuration: 3RS, 6SR
Crystal form: light brown solid
Melting point: 151.5–153.5° C.
Salt form: free Example 30

Structures of substituents

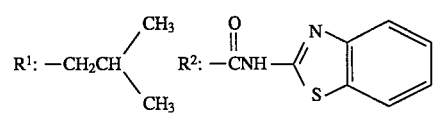

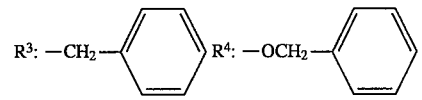

Configuration: 3RS, 6SR
Crystal form: white solid
Salt form: free

Example 31

Structures of substituents

TABLE 8-continued

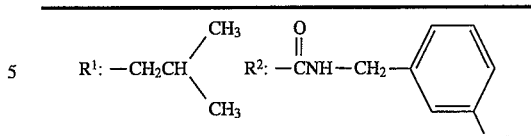

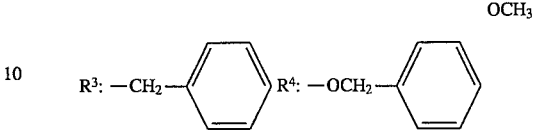

Configuration: 3RS, 6SR
Crystal form: white solid
Salt form: free

TABLE 9

Example 32

Structures of substituents

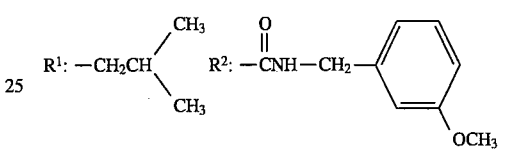

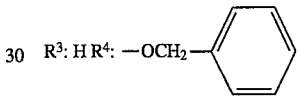

Configuration: Mixture of 3RS, 6SR and 3RS, 6RS
Crystal form: light brown solid
Salt form: free Example 33

Structures of substituents

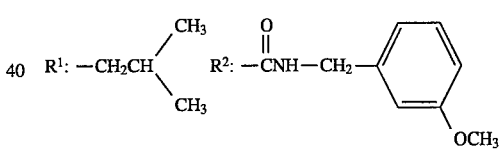

$R^3$: H  $R^4$: —OH
Configuration: 3RS, 6SR
Crystal form: white solid (recrystallized from ethyl acetate-n-hexane)
Melting point: 141.5–143.5° C.
Salt form: free Example 34

Structures of substituents

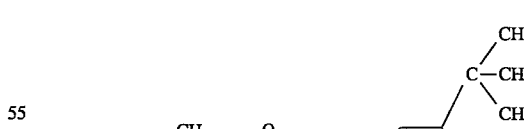
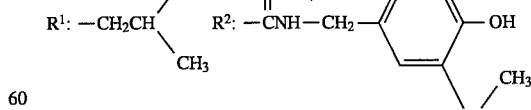

TABLE 9-continued

R³: H R⁴: —OCH₂— 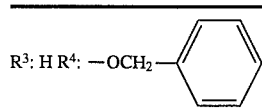

Configuration: 3RS, 6SR
Crystal form: colorless prisms (recrystallized from diisopropyl ether)
Salt form: free

TABLE 10

Example 35

Structures of substituents

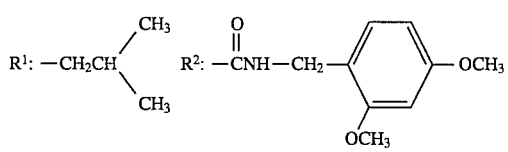

R³: H

R⁴: —OCH₂— 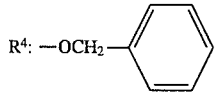

| | |
|---|---|
| Configuration: | Mixture of 3RS, 6SR and 3RS, 6RS |
| Crystal form: | white solid (recrystallized from ethanol) |
| Salt form: | free |

Example 36

Structures of substituents

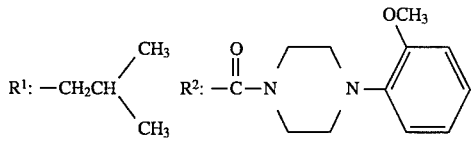

R³: H

R⁴: —OCH₂— 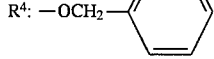

| | |
|---|---|
| Configuration: | Mixture of 3RS, 6SR and 3RS, 6RS |
| Crystal form: | white foam-like substance |
| Salt form: | free |

Example 37

Structures of substituents

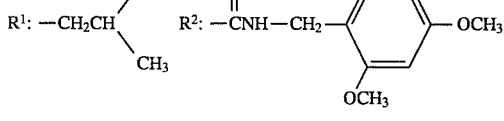

| | |
|---|---|
| R³: H | R⁴: —OH |
| Configuration: | 3RS, 6SR |
| Crystal form: | colorless needles (recrystallized from ethyl acetate) |
| Melting point: | 140.5–141.5° C. |
| Salt form: | free |

TABLE 11

Example 38

Structures of substituents

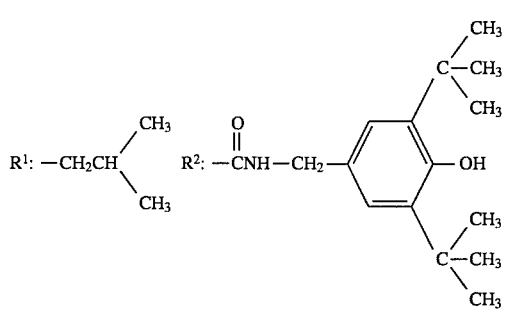

| | |
|---|---|
| R³: H | R⁴: —OH |
| Configuration: | 3RS, 6SR |
| Crystal form: | colorless needles (recrystallized from ethyl acetate-n-hexane) |
| Melting point: | 146.5–150° C. |
| Salt form: | free |

Example 39

Structures of substituents

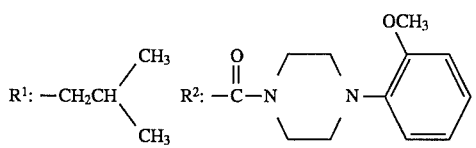

| | |
|---|---|
| R³: H | R⁴: —OH |
| Configuration: | 3RS, 6SR |
| Crystal form: | colorless prisms (recrystallized from ethanol-ethyl acetate) |
| Melting point: | 165–167.5° C. |
| Salt form: | hydrochloride |

Example 40

Structures of substituents

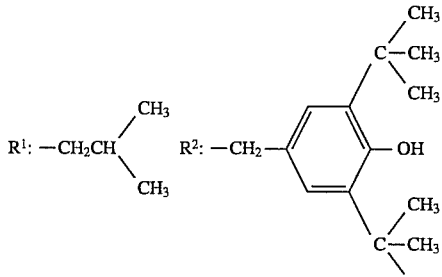

R³: H

R⁴: —OCH₂— 

| | |
|---|---|
| Configuration: | 3RS, 6RS |
| Crystal form: | colorless needles (recrystallized from ethyl acetate) |
| Melting point: | 198.5–200.5° C. (decomp.) |
| Salt form: | free |

TABLE 12

Example 41

Structures of substituents

TABLE 12-continued

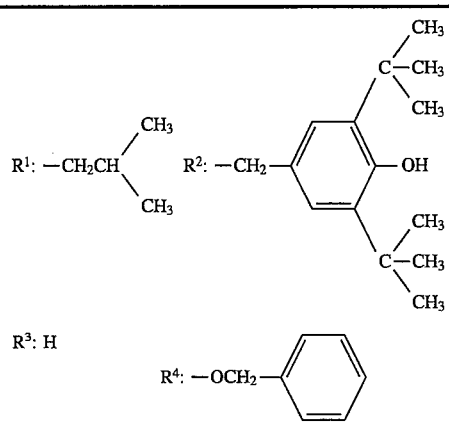

| Configuration: | 3RS, 6SR |
|---|---|
| Crystal form: | light yellow solid |
| Salt form: | free |

Example 42

Structures of substituents

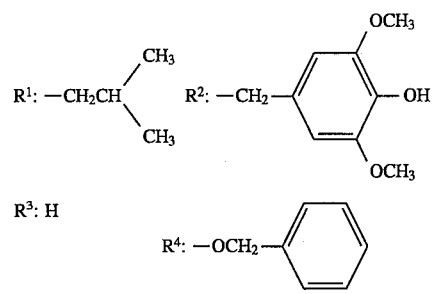

| Configuration: | 3RS, 6RS |
|---|---|
| Crystal form: | light yellow foam-like substance |
| Salt form: | free |

Example 43

Structures of substituents

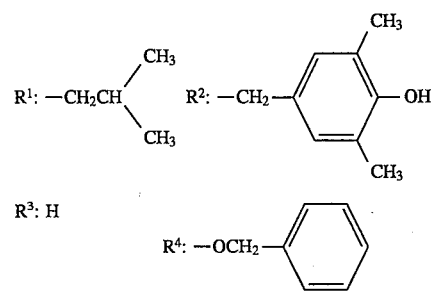

| Configuration: | 3RS, 6RS |
|---|---|
| Crystal form: | brown foam-like substance |
| Salt form: | free |

TABLE 13

Example 44

Structures of substituents

TABLE 13-continued

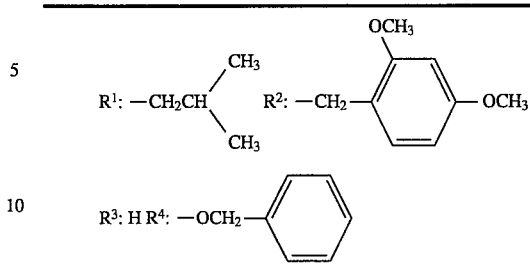

| Configuration: | 3RS, 6RS |
|---|---|
| Crystal form: | yellow vitreous substance |
| Salt form: | free |

Example 45

Structures of substituents

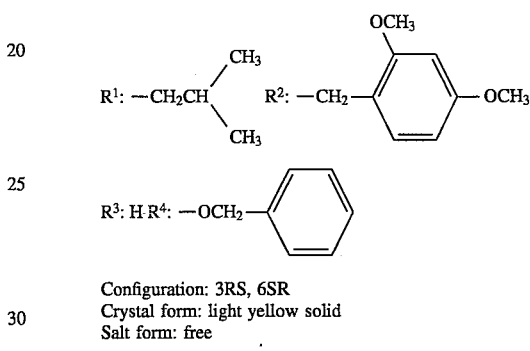

| Configuration: | 3RS, 6SR |
|---|---|
| Crystal form: | light yellow solid |
| Salt form: | free |

EXAMPLE 46

1.24 g of dicyclohexylcarbodiimide was added to 30 ml of 2.04 g of (3RS,6SR)-3-carboxy-6-isobutyl-3-methyl-1-(2-tetrahydropyranyloxy)piperazine-2,5-dione and 0.73 g of N-hydroxysuccinimide in anhydrous dioxane. The mixture was stirred at room temperature for 3 hours. The reaction mixture was filtered to remove the insoluble materials. To the filtrate was added 0.84 ml of 3-methoxybenzylamine. The mixture was stirred at room temperature for 19 hours. The reaction mixture was diluted with 150 ml of ethyl acetate. The resulting solution was washed with an aqueous solution saturated with sodium hydrogencarbonate and an aqueous solution saturated with sodium chloride, then dried with anhydrous magnesium sulfate, and subjected to distillation to remove the solvent, to obtain 3.32 g of (3RS,6SR)-1-(2-tetrahydropyranyloxy)-6-isobutyl-3-[N-(3-methoxybenzyl)]carbamoyl-3-methylpierazine-2,5-dione as a yellow oily substance.

By using suitable starting materials and by employing the same manners as in Examples 4, 5, 6 and 8, there were obtained the compounds of Examples 47–65 shown in the following Tables 14–19.

TABLE 14

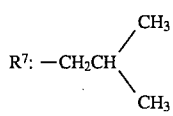

Example 47

Structures of substituents

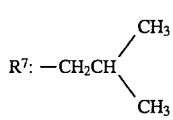

R⁸: H  R⁹: —OH
Configuration: 2S, 6S
Crystal form: light orange solid (recrystallized from chloroform-n-hexane)
Melting point: 146–148° C. (decomp.)
Salt form: free Example 48

Structures of substituents

R⁷: —CH₂CH(CH₃)CH₃ [as shown in image]

R⁸: H  R⁹: —OH
Configuration: 3S, 6R
Crystal form: light orange solid
Melting point: 128–129.5° C. (decomp.)
Salt form: free

TABLE 15

Example 49

Structures of substituents

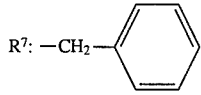

R⁸: H  R⁹: —OH
Configuration: 3S, 6S
Crystal form: light orange solid (recrystallized benzene)
Melting point: 119–121° C. (decomp.)
Salt form: free Example 50

Structures of substituents

R⁷: —CH₂—phenyl

R⁸: H  R⁹: —OH
Configuration: 3S, 6R
Crystal form: light orange solid (recrystallized from benzene)
Melting point: 219.5–222° C.
Salt form: free TABLE 15-continued Example 51

Structures of substituents
R⁷: —CH₂CH₂SCH₃  R⁸: H  R⁹: —OH
Configuration: 3S, 6S
Crystal form: light brown solid (recrystallized from benzene)
Melting point: 129.5–134.5° C. (decomp.)
Salt form: free Example 52

Structures of substituents
R⁷: —CH₂CH₂SCH₃  R⁸: H  R⁹: —OH
Configuration: 3S, 6R
Crystal form: light brown solid (recrystallized from benzene)
Melting point: 170.5–173.5° C. (decomp.)
Salt form: free

TABLE 16

Example 53

Structures of substituents

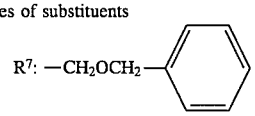

R⁸ : H
R⁹ : —OH
Configuration: 3S, 6S
Crystal form: white solid
Melting point: 196–197.5° C. (decomp.)
Salt form: free Example 54

Structures of substituents

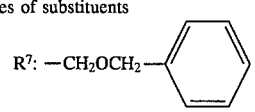

R⁸ : H
R⁹ : —OH
Configuration: 3S, 6R
Crystal form: orange solid (recrystallized from benzene)
Melting point: 180.5–182° C.
Salt form: free Example 55

Structures of substituents
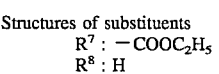
Configuration: 3RS, 6SR
Crystal form: white solid (recrystallized from dichloromethane-methanol)
Melting point: 166.5–167.5° C.
Salt form: free Example 56

Structures of substituents
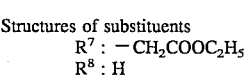
Configuration: 3S, 6S
Crystal form: colorless prisms (recrystallized from isopropyl alcohol-diisopropyl ether)
Melting point: 183.5–185.5° C. (decomp.)
Salt form: free

TABLE 17

Example 57

Structures of substituents
 $R^7$ : —CH$_2$COOC$_2$H$_5$
 $R^8$ : H
 $R^9$ : —OH
Configuration: 3S, 6R
Crystal form: brown prisms (recrystallized from isopropyl alcohol)
Melting point: 172–172.5° C.
Salt form: free Example 58

Structures of substituents

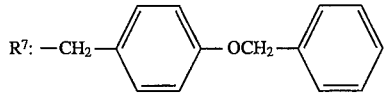

$R^8$ : H
 $R^9$ : —OH
Configuration: 3S, 6S
Crystal form: brown vitreous substance
Salt form: free Example 59

Structures of substituents

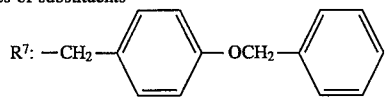

$R^8$ : H
 $R^9$ : —OH
Configuration: 3S, 6R
Crystal form: brown solid
Salt form: free Example 60

Structures of substituents

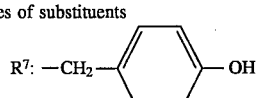

$R^8$ : H
 $R^9$ : —OH
Configuration; 3S, 6S
Crystal form: colorless vitreous substance
Salt form: free

TABLE 18

Example 61

Structures of substituents

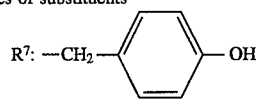

$R^8$ : H
 $R^9$ : —OH
Configuration: 3S, 6R
Crystal form: white solid (recrystallized from diethyl ether-n-hexane)
Melting point: 188.5–191.5° C. (decomp.)
Salt form: free Example 62

Structures of substituents
 $R^7$ : —CH$_2$OH
 $R^8$ : H
 $R^9$ : —OH
Configuration: 3S, 6R
Crystal form: light red solid (recrystallized from dichloromethane)

TABLE 18-continued

Melting point: 228.5–230° C. (decomp.)
Salt form: free

Example 63

Structures of substituents
 $R^7$ : —CH$_2$OH
 $R^8$ : H

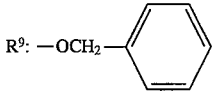

Configuration: 3S, 6RS
Crystal form: light yellow foam-like substance
Salt form: free

TABLE 19

Example 64

Structures of substituents
 $R^7$ & $R^8$: —(CH$_2$)$_3$—
 $R^9$: —OH
Configuration: 3S, 6S
Crystal form: colorless columns (recrystallized from methanol)
Melting point: 238–241° C. (decomp.)
Salt form: free Example 65

Structures of substituents
 $R^7$: —CH$_2$OH
 $R^8$: H
 $R^9$: —OH
Configuration: 3S, 6S
Crystal form: light yellow foam-like substance
Salt form: free The NMR spectral data of part of the compounds obtained above are shown in the following Tables 20–25.

TABLE 20

| Example | Solvent | $^1$H—NMR (250 MHz) δ ppm |
|---|---|---|
| 23 | DMSO-d$_6$ | 0.30–0.50(1H, m), 0.62(3H, d, J=6Hz), 0.64(3H, d, J=6Hz), 0.70–0.85 (1H, m), 1.45–1.75(1H, m), 2.76(1H, dd, J=5Hz, J=14Hz), 3.06(1H, dd, J=3Hz, J=14Hz), 3.71(1H, dd, J=5.5Hz, J=7.5Hz), 4.21(1H, s-like), 5.00(2H, s), 6.91, 7.02(each 2H, d, J=8.5Hz), 7.25–7.50(5H, m), 8.26(1H, s), 9.91 (1H, s) |
| 24 | DMSO-d$_6$ | 0.80(3H, d, J=6Hz), 0.82(3H, d, J=6Hz), 1.50–1.90(3H, m), 2.82(1H, dd, J=4.5Hz, J=13.5Hz), 3.00–3.25(1H, m), 3.42(1H, t, J=5Hz), 4.29(1H, s-like), 5.03(2H, s), 6.88, 7.11(each 2H, d, J=8.5Hz), 7.25–7.55(5H, m), 8.25(1H, brs), 9.87(1H, s) |
| 25 | DMSO-d$_6$ | 0.75(6H, d, J=6.5Hz), 1.00–1.20(2H, m), 1.20–1.40(1H, m), 2.88(2H, d, J=5Hz), 3.88(1H, dd, J=5Hz, 6.5Hz), 4.10–4.15(1H, m), 5.13(2H, s), 6.95 (1H, s), 7.20–7.45(5H, m), 7.81(1H, s), 8.13(1H, s), 10.12(1H, brs) |
| 30 | CDCl$_3$ | 0.75(3H, d, J=6Hz), 0.76(3H, d, J=6Hz), 1.50–1.85(3H, m), 3.26, 3.64 (each 1H, d, J=13.5Hz), 3.51(1H, t, J=6Hz), 4.49, 4.81(each 1H, d, J=10Hz), 6.95(1H, brs), 7.10–7.20 (2H, m), 7.25–7–40(9H, m), 7.48(1H, t, J=8Hz), 7.85(2H, t, J=8Hz) |

TABLE 21

| Example | Solvent | $^1$H—NMR (250 MHz) δ ppm |
|---|---|---|
| 31 | CDCl$_3$ | 0.73(3H, d, J=6Hz), 0.74(3H, d, J=6Hz), 1.55–1.70(3H, m), 3.15, 3.52 (each 1H, d, J=13.5Hz), 3.46(1H, t, J=4.5Hz), 3.79(3H, s), 4.43(1H, dd, J=5.5Hz, J=15Hz), 4.51(1H, dd, J=5.5Hz, J=15Hz), 4.35, 4.71(each 1H, d, J=10.5Hz), 6.75–6.95(4H, m), 7.05–7.15(2H, m), 7.15–7.40(8H, m), 8.16 (1H, t, J=5.5Hz) |
| 32 | CDCl$_3$ | 0.85(1.5H, d, J=6.5Hz), 0.86(1.5H, d, J=6.5Hz), 0.92(3H, d, J=6Hz), 1.60–2.00(3H, m), 3.78(1.5H, s), 3.80(1.5H, s), 4.00(1H, t, J=6Hz), 4.43(1H, d, J=6Hz), 4.46(0.5H, d, J=6Hz), 4.53(0.5H, d, J=6Hz), 4.54 (0.5H, s-like), 4.62(0.5H, d, J=2.5Hz), 4.88, 4.99(each 0.5H, d, J=10.5Hz), 4.95, 5.01(each 0.5H, d, J=10.5Hz), 6.46(0.5H, brs), 6.90 (0.5H, brs), 6.70–7.00(3H, m), 7.15–7.28(1H, m), 7.37(2.5H, s), 7.40 (2.5H, s), 7.54(0.5H, brt, J=6Hz), 8.53(0.5H, brt, J=6Hz) |
| 34 | CDCl$_3$ | 0.85(3H, d, J=6.5Hz), 0.86(3H, d, J=6Hz), 1.42(18H, s), 1.65–1.75(2H, m), 1.75–1.95(1H, m), 4.00(1H, t, J=6Hz), 4.27(1H, dd, J=5Hz, J=14Hz), 4.45(1H, dd, J=6Hz, J=14Hz), 4.59 (1H, d, J=2.5Hz), 4.94, 5.01(each 1H, d, J=10.5Hz), 5.21(1H, s), 6.33(1H, brs), 7.05(2H, s), 7.30–7.40(1H, br), 7.40(5H, s) |

TABLE 22

| Example | Solvent | $^1$H—NMR (250 MHz) δ ppm |
|---|---|---|
| 35 | DMSO-d$_6$ | 0.75–0.95(6H, m), 1.60–1.95(3H, m), 3.72(2.4H, s), 3.73(0.6H, s), 3.77 (0.6H, s), 3.79(2.4H, s), 4.00–4.30 (2H, m), 4.34(1H, t, J=5Hz), 4.66 (1H, s-like), 4.80, 4.91(each 1H, d, J=10Hz), 6.46(1H, dd, J=2.5Hz, J=8.5Hz), 6.54(1H, d, J=2.5Hz), 7.11 (0.2H, d, J=8.5Hz), 7.20(0.8H, d, J=8.5Hz), 7.35–7.50(5H, m), 8.24 (0.2H, brs), 8.44(0.2H, brs), 8.52 (0.8, brs), 8.66(0.8H, brt, J=6Hz) |
| 36 | CDCl$_3$ | 0.90(3H, d, J=6Hz), 0.92(3H, d, J=6Hz), 1.65–2.15(3H, m), 2.80–3.30 (4H, m), 3.50–3.65(1H, m), 3.65–3.85 (1H, m), 3.88(3H, s), 4.04(1H, t, J=6.5Hz), 3.95–4.35(2H, m), 4.95, 5.02(each 1H, d, J=10Hz), 5.16(1H, d, J=3Hz), 6.50–6.60(1H, m), 6.85–7.00(3H, m), 7.00–7.15(1H, m), 7.30–7.50(5H, m) |
| 41 | CDCl$_3$ | 0.86(3H, d, J=6Hz), 0.88(3H, d, J=6Hz), 1.43(18H, s), 1.60–1.95(3H, m), 2.74(1H, dd, J=9.5Hz, J=14Hz), 3.44(1H, dd, J=3.5Hz, J=14Hz), 3.77 (1H, t, J=6Hz), 4.15(1H, dd, J=3.5Hz, J=9.5Hz), 4.82, 4.97(each 1H, d, J=10.5Hz), 5.21(1H, s), 5.67(1H, brs), 7.01(2H, s), 7.37(5H, s) |

TABLE 23

| Example | Solvent | $^1$H—NMR (250 MHz) δ ppm |
|---|---|---|
| 42 | CDCl$_3$ | 0.81(3H, d, J=6.5Hz), 0.82(3H, d, J=6.5Hz), 0.98–1.14(1H, m), 1.26–1.42 (1H, m), 1.70–1.92(1H, m), 3.00(1H, dd, J=7.5Hz, J=14Hz), 3,14(1H, dd, J=4Hz, J=14Hz), 3.85(6H, s), 3.79–3.93(1H, m), 4.22–4.35(1H, m), 4.97, 5.03(each 1H, d, J=10.5Hz), 5.50(1H, s), 5.97–6.25(1H, br), 6.40(2H, s), 7.35–7.50(5H, m) |
| 43 | DMSO-d$_6$ | 0.20–0.40(1H, m), 0.59(3H, d, J=6.5Hz), 0.61(3H, d, J=6.5Hz), 0.55–0.70(1H, m), 1.35–1.55(1H, m), 2.06 (6H, s), 2.65(1H, dd, J=4.5Hz, J=14Hz), 2.99(1H, dd, J=3Hz, J=14Hz), 3.76(1H, t, J=6.5Hz), 4.22(1H, s-like), 4.78, 4,92(each 1H, d, J=10Hz), 6.62(2H, s), 7.37(5H, s), 8.08(1H, s), 8.27(1H, brs) |
| 44 | CDCl$_3$ | 0.84(6h, d, J=6.5Hz), 1.15–1.35(1H, m), 1.40–1.55(1H, m), 1.75–1.95(1H, m), 2.92(1H, dd, J=8Hz, J=13.5Hz), 3.36(1H, dd, J=4.5Hz, J=13.5Hz), 3.78 (3H, s), 3.80(3H, s), 3.88(1H, dd, J=5.5Hz, J=8Hz), 4.20–4.35(1H, m), 4.94, 5.02(each 1H, d, J=10.5Hz), 5.65(1H, brs), 6.41(1H, dd, J=2.5Hz, J=8Hz), 6.45(1H, d, J=2.5Hz), 7.04 (1H, d, J=8Hz), 7.30–7.50(5H, m) |

TABLE 24

| Example | Solvent | $^1$H—NMR (250 MHz) δ ppm |
|---|---|---|
| 45 | CDCl$_3$ | 0.86(3H, d, J=6.5Hz), 0.87(3H, d, J=6.5Hz), 1.50–1.90(3H, m), 2.93(1H, dd, J=7.5Hz, J=14Hz), 3.51(1H, dd, J=4Hz, J=14Hz), 3.75(1H, t, J=6Hz), 3.80(3H, s), 3.85(3H, s), 4.23(1H, dd, J=4Hz, J=7.5Hz), 4.82, 4.97(each 1H, d, J=11Hz), 6.00(1H, brs), 6.47 (1H, d, J=2.5Hz, J=8Hz), 6.50(1H, d, J=2.5Hz), 7.15(1H, d, J=8Hz), 7.25–7.40(5H, m) |
| 58 | DMSO-d$_6$ | 0.80(1H, dd, J=9.5Hz, J=13Hz), 2.22 (1H, dd, J=3.5Hz, J=13Hz), 3.00–3.55 (2H, m), 3.60–3.75(1H, m), 4.08, 4.13 (each 1H, d, J=3.5Hz), 4.30(1H, s-like), 6.19, 6.69(each 1H, d, J=8.5Hz), 7.01(1H, t, J=7.5Hz), 7.10 (1H, t, J=7.5Hz), 7.17(1H, d, J=2Hz), 7.25–7.50(6H, m), 7.56(1H, s), 7.57 (1H, d, J=8Hz), 10.22(1H, brs), 11.00 (1H, brs) |
| 59 | DMSO-d$_6$ | 2.40–2.60(1H, m), 2.81(1H, d-like, J=4Hz), 2.87(1H, dd, J=4Hz, J=14Hz), 3.18(1H, dd, J=4Hz, J=15Hz), 3.28 (1H, dd, J=4Hz, J=15Hz), 3.93(1H, s-like), 6.82, 6.97(each 2H, d, J=8.5Hz), 6.90–7.10(3H, m), 7.25–7.50 (6H, m), 7.49(1H, d, J=8Hz), 7.94 (1H, s), 10.00(1H, s), 10.94(1H, brs) |

TABLE 25

| Example | Solvent | $^1$H—NMR (250 MHz) δ ppm |
|---|---|---|
| 60 | DMSO-d$_6$ | 0.75(1H, dd, J=9.5Hz, J=13Hz), 2.21 (1H, dd, J=4Hz, J=13.5Hz), 3.08(1H, dd, J=5Hz, J=15Hz), 3.15–3.30(1H, m), 3.55–3.75(1H, m), 4.28(1H, s-like), 6.06, 6.44(each 2H, d, J=8.5Hz), 6.90–7.15(2H, m), 7.16(1H, s), 7.31 (1H, d, J=8Hz), 7.48(1H, d, J=2.5Hz), 7.57(1H, d, J=8Hz), 9.08(1H, s), 10.21(1H, brs), 10.98(1H, brs) |
| 63 | CDCl$_3$ | 1.65–1.70(0.5H, m), 2.37(0.5H, t, J=6Hz), 2.85–3.00(0.5H, m), 3.30–3.60 |

TABLE 25-continued

| Example | Solvent | $^1$H—NMR (250 MHz) δ ppm |
|---------|---------|---------------------------|
|  |  | (3H, m), 3.70–3.85(0.5H, m), 4.21 (0.5H, s-like), 4.30(0.5H, s-like), 4.91, 5.04(each 1H, d, J=11Hz), 4.96, 5.13(each 1H, d, J=10.5Hz), 6.32 (0.5H, brs), 6.75(0.5H, brs), 6.95 (1H, d, J=2Hz), 7.02(1H, t, J=7.5Hz), 7.11(1H, t, J=7.5Hz), 7.27(1H, d, J=7.5Hz), 7.32–7.52(6H, m), 7.50–7.65 (1H, m), 8.77(1H, brs) |
| 65 | DMSO-d$_6$ | 2.19(1H, dd, J=7Hz, 11Hz), 3.08(1H, dd, J=3Hz, J=11Hz), 3.31(2H, d, J=4Hz), 3.60–3.75(1H, m), 4.32(1H, t, J=4Hz), 4.60(1H, brs), 6.93(1H, t, J=7.5Hz), 7.03(1H, t, J=5Hz), 7,07 (1H, d, J=2Hz), 7.31(1H, d, J=8Hz), 7.52(1H, d, J=8Hz), 7.95(1H, brd. J=2Hz), 10.03(1H, brs), 10.88(1H, brs) |

Pharmacological Test—1

Inhibitory effect against superoxide radicals (O$_2^-$) released from the peritoneal macrophage cells of guinea pig by stimulation:

Mineral oil (15 ml)was intraperitoneally administered to a guinea pig, then 96 hours after the administration, the peritoneal macrophage cells were sampled.

Superoxide radicals (O$_2^-$) were determined by means of reduction of cytochrome C method according to the procedure described in an article written by T. Matsumoto, K. Takeshige and S. Minakami: Biochemical and Biophysical Research Communications, Vol. 88, No. 3, pp. 974–979, (1979).

Into 1 ml of 80 μM-cytochrome C solution, the peritoneal macrophage cells were added to make the final concentration of 2×10$^6$ cells/ml, then each one of the test compounds of the present invention was added thereto to make the test group sample. On the other hand, water was added in place of the test compound of the present invention to make the control group sample. Each of the test group samples and the control group samples were subjected to pre-incubation at 37° C. for 1 minute.

As to the stimulating agent for releasing superoxide radicals (O$_2^-$), FMLP (formylmethionyl leucyl phenylalanine)was added to each one of the test sample solutions and the control group samples to make the final concentration of FMLP to 10$^{-7}$M, then the sample solutions were subjected to additional reaction by incubation for 1 minute.

Difference between the optical absorbances measured at 550 nm (OD$_{550}$) of both test group samples and control group samples were determined, the 50% inhibitory concentration (IC$_{50}$) was obtained by calculating as the ratio of OD$_{550}$ of the test group sample to that of the control group sample. The IC$_{50}$ (×10$^{-5}$ g/ml) obtained from the test are shown in Table 26 as follows:

TABLE 26

| Test compound No. | IC$_{50}$ (×10$^{-5}$ g/ml) | Test compound No. | IC$_{50}$ (×10$^{-5}$ g/ml) |
|---|---|---|---|
| Compound of: |  | Compound of: |  |
| Example 10 | 1.8 | Example 28 | 0.3 |
| Example 12 | 1.5 | Example 29 | 0.3 |
| Example 13 | 0.13 | Example 47 | 1.0 |
| Example 16 | 3.0 | Example 49 | 1.0 |

TABLE 26-continued

| Test compound No. | IC$_{50}$ (×10$^{-5}$ g/ml) | Test compound No. | IC$_{50}$ (×10$^{-5}$ g/ml) |
|---|---|---|---|
| Example 19 | 3.0 | Example 51 | 0.3 |
| Example 20 | 3.0 | Example 52 | 0.6 |
| Example 26 | 0.6 | Example 53 | 3.0 |
| Example 27 | 0.025 | Example 60 | 1.0 |

Pharmacological Test—2

Inhibitory effect against the releasing of lysozomal enzyme from the neutrocytes of rat The neutrocytes of rat were samples from the abdominal cavity of rat 16 hours after the administration of 10 ml of 1% casein solution (physiological saline solution).

Reaction of the releasing of lysozomal enzyme from the neutrocytes of rat was determined by means of the method as described in an article written by T. Matsumoto, K. Takeshige and S. Minakami: Biochemical and Biophysical Research Communications, Vol. 88, No. 3, pp 974–979, (1979).

The neutrocytes being sampled were added to Hank's solution so as to make the concentration thereof as 5×10$^5$ cells/ml, the test compound of piperazine derivative of the present invention was added thereto to make the test group sample. On the other hand, water was added in place of the piperazine derivative of the present invention to make the control group sample. Each of the test group samples and the control group samples were subjected to pre-incubation at 37° C. for 1 minute.

As to the stimulating agents, 10$^{-6}$M of FMLP (formylmethionyl leucyl phenylalanine) and 5 μg/ml of cytocharasin B solution were added to the test solutions. Thus obtained mixture of the solution was reacted by incubating for 15 minutes. After the incubation, the mixture of the solution was subjected to centrifugation at 2,000 rpm for 10 minutes. The supernatant (0.2 ml) was admixed with 0.5 ml of 0.1 M-acetic acid buffer solution (pH 4.5) in which 0.2 mM of phenolphthalein glucuronic acid was dissolved. Then the resulting mixture of the solution was reacted at 37° C. for 5 hours by incubation. After the reaction, 1N-NaOH solution was added to the reaction mixture so as to make the pH value thereof to pH 8 to 9, and the optical absorbance of both test group samples and control group samples were determined at 540 nm (OD$_{540}$).

The 50% inhibitory concentration (IC$_{50}$) values were obtained by calculation as the ratio of OD$_{540}$ of the test group sample to that of the control group sample. The IC$_{50}$ (×10$^{-5}$ g/ml) values obtained from the test are shown in Table 27 below.

TABLE 27

| Test compound No. | IC$_{50}$ (10$^{-5}$ g/ml) |
|---|---|
| Compound of: |  |
| Example 20 | 3.0 |
| Example 27 | 0.3 |
| Example 28 | 0.3 |
| Example 29 | 0.2 |

Pharmacological Test—3

Inhibitory effect against the releasing of hydrogen peroxide (H$_2$O$_2$) from the neutrocyte of abdominal cavity of rat 1%-Casein solution was administered to the abdominal cavity of a SD-strain rat, then 16 hours after the administration, the neutrocytes were obtained by washing the abdominal cavity. Thus obtained neutrocytes were washed with Hank's solution.

In to a reaction mixture consisting of the following ingredients:

| | |
|---|---|
| NaN$_3$ | 1 mM |
| NaCl | 140 mM |
| KCl | 5 mM |
| MgCl$_2$ | 1 mM |
| CaCl$_2$ | 1 mM |
| Glucose | 5.5 mM |
| Phenol red | 0.28 mM |
| HRP (Horse Radish peroxide) | 8.5 U/ml |
| HEPES [N-(2-Hydroxyethyl)piperazine N'-2-ethanesulfonic acid] | 10 mM (pH 7.0) |
| Rat neutrocytes | 10$^6$ cells/ml |
| FMLP | 2 × 10$^{-6}$ M | the test compound was added, then the whole mixture was incubated at 37° C. for 1 hour, and the mixture was subjected to a centrifugal separation at 2,000 rpm for minutes. After the centrifugal separation, 1 ml of the supernatant was sampled and 10 μl of 1N-NaOH aqueous solution was added thereto. Then, the optical absorbance at 610 nm (OD$_{610}$) of the supernatant was determined by means of using a spectrophotometer.

The IC$_{50}$ (50% inhibitory concentration) of the test compound was obtained by calculating as the ratio of OD$_{610}$ of the test group sample to that of the control group sample. The results are indicated in Table 28 as follows:

TABLE 28

| Test compound No. | IC$_{50}$ (10$^{-5}$ g/ml) | Test compound No. | IC$_{50}$ (10$^{-5}$ g/ml) |
|---|---|---|---|
| Compound of: | | Compound of: | |
| Example 9 | <0.6 | Example 29 | 0.5 |
| Example 11 | 0.6 | Example 48 | <0.3 |
| Example 13 | <0.5 | Example 49 | <0.3 |
| Example 15 | <0.3 | Example 50 | <0.3 |
| Example 16 | <0.3 | Example 51 | 0.3 |
| Example 17 | <0.3 | Example 54 | 0.3 |
| Example 18 | 0.5 | Example 55 | 0.3 |
| Example 19 | 0.5 | Example 57 | 0.3 |
| Example 21 | 1.0 | Example 60 | 0.6 |
| Example 26 | 0.3 | Example 64 | <0.3 |

Pharmacological Test—4

Inhibitory effect against increase of urinary proteins in the passive Heymann nephritis of rat SD-strain male rats (7 week old, body weight: 200–230 g) were used as test animals.

An antiserum which will induce passive Heymann nephritis of rat was prepared by procedures according to the method of T. S. Edington, et al. [T. S. Edington, R. J. Glassock and F. J. Dixon: Autologous immune complex nephritis induced with renal tublar antigen. I. Identification and isolation of the pathogenetic antigen. Journal of Experimental Medicine Vol. 127, pp. 555–572 (1968).] as follows:

At the first, an antigen (FX1A fraction) of the renaltublar brush border was sampled from the SD rat. Next, the antigen was admixed with Freund' complete adjuvant, then a New Zealand White rabbit was sensitized therewith. The sensitization procedures were conducted 3 times in every 2 weeks, and 2 weeks after the final sensitization, the blood sample was obtained from the rabbit.

The test rats were divided into test groups depend on their body weight, each of which is consisting of 7 rats.

Heymann nephritis of the rats were induced by injecting the above-mentioned antiserum to the tail vein of the test rats. Each one of the test compounds was suspended in 0.5%-CMC (carboxymethylcellulose) aqueous solution, and said test compound suspension was orally administered once a day from the fourth day after the injection, for 7 days continuously. The urine samples of the rat were taken in time sequentially from the 10th day after the injection, and the amount of urinary protein in the samples were determined. The rate of inhibitory effect (%) against the production of urinary protein performed by the test compound was calculated by the formula as follows:

Rate of inhibition effect (%)=[(A−B)/(A)]×100 wherein

A: the amount of urinary protein in the control group;

B: the amount of urinary protein in the test group (in the case that test compound was administered).

The test results are shown in Table 29 as follows:

TABLE 29

| Test compound No. | Dose (mg/kg/day) | Rate of inhibitory effect (%) (12th day) |
|---|---|---|
| Compound of: | | |
| Example 13 | 20 | 57.8 ± 6.1 |
| Example 57 | 5 | 53.1 ± 15.1 |

Pharmacological Test—5

Inhibitory effects on rat mesangial cell proliferation

The kidney of SD-strain rat was aseptically taken out by excision, and the renal cortex was cut out therefrom. The renal glomeruli were isolated by use of sieve. The glomeruli were cultivated in RPMI1640 culture medium [which contains 10% of FBS (fetal bovine serum)] for 4 weeks. Thus obtained cells were used as mesangial cells.

An experiment of incorporation of thymidine by interleukin-1β was conducted by procedures according to the method of Ganz [Michael B. Ganz; Mary C. Perfetto and Walter F. Boron: American Journal of Physiology, Vol. 259, F269-F278, (1990)]. Thus, 2×10$^4$ cells/ml of mesangial cells were scattered on a 48-well plate (0.5 ml/well), and the cells were cultivated in RPMI culture medium (which contains 10% of FBS) for 3 days. Then, the culture medium was changed to another RPMI culture medium in which the concentration of FBS was decreased from 10% to 0.5% and cultivated for 3 days. Next, the RPMI culture medium (containing 0.5% of FBS) was changed to other RPMI culture medium to which the test compound and 1 ng/ml of interleukin-1β were added. The cultivation was conducted for 24 hours, then 1 μCi/well of 3H-thymidine was added to the culture medium, and the cultivation was continued for additional 24 hours.

The amount of $^3$H-thymidine being incorporated into the mesangial cells was measured by use of a scintillation counter, and the rate of inhibition (%) in comparison of the test group vs. control group was calculated by the following formula:

Rate of inhibition (%)=[(C−D)/(C−E)]×100 wherein

C: the incorporated amount of $^3$H-thymidine in control group;

D: the incorporated amount of $^3$H-thymidine in the case of that test compound was added;

E: the incorporated amount of $^3$H-thymidine in the case of that interleukin-1β was not added.

The test results are shown in the following Table 30.

TABLE 30

| Test compound | Concentration | Rate of inhibition (%) |
|---|---|---|
| Compound of: | | |
| Example 13 | 10 μg/ml | 121.5 ± 6.1 |
|  | 3 μg/ml | 77.9 ± 8.3 |
| Example 57 | 10 μg/ml | 56.7 ± 2.9 |
|  | 3 μg/ml | 26.3 ± 5.8 |

We claim:

1. A piperazine compound having the general formula (1):

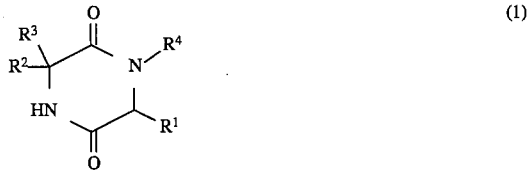

(1)

wherein $R^1$ is a lower alkyl group;

$R^2$ is a phenyl-lower alkyl group which may have, on the phenyl ring, 1 to 3 substituents selected from the group consisting of a hydroxyl group, a phenyl-lower alkoxy group, a lower alkyl group, a lower alkoxy group and a halogen atom, an imidazolyl-substituted lower alkyl group which may have one or more phenyl-lower alkyl groups as substituents on the imidazolyl ring, or a group of the formula:

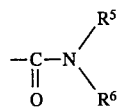

(wherein $R^5$ and $R^6$ are the same or different, and are each a hydrogen atom, a benzothiazolyl group, or a phenyl-lower alkyl group which may have, on the phenyl ring, 1 to 3 substituents selected from the group consisting of a lower alkoxy group, a phenyl-lower alkoxy group, a lower alkyl group and a hydroxyl group, further, said $R^5$ and $R^6$ and the adjacent nitrogen atom being bonded thereto, together with or without another nitrogen atom or an oxygen atom, may form a 5- to 6-membered saturated heterocyclic group; said heterocyclic group may have, as substituents, one or more phenyl groups which may have one or more lower alkoxy groups as substituents on the phenyl ring);

$R^3$ is a hydrogen atom, a lower alkyl group or a phenyl-lower alkyl group; and $R^4$ is a hydroxyl group, a phenyl-lower alkoxy group or a tetrahydropyranyloxy group;

and pharmaceutically acceptable salts thereof.

2. A piperazine compound having the general formula (2):

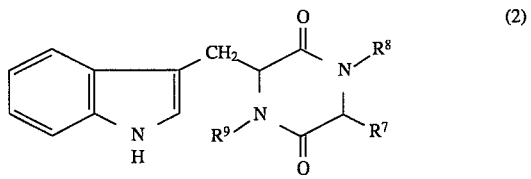

(2)

wherein $R^7$ is a lower alkyl group, a phenyl-lower alkyl group which may have, on the phenyl ring, one or more substituents selected from the group consisting of a hydroxyl group and a phenyl-lower alkoxy group, a lower alkylthio group- substituted lower alkyl group, a phenyl-lower alkoxy group- substituted lower alkyl group, a lower alkoxycarbonyl group, a lower alkoxycarbonyl group- substituted lower alkyl group or a hydroxyl group-substituted lower alkyl group;

$R^8$ is a hydrogen atom; further $R^7$ and $R^8$ may form a trimethylene group by combining together; and $R^9$ is a hydroxyl group or a phenyl-lower alkoxy group; and pharmaceutically acceptable salts thereof.

3. The piperazine compound or salt thereof according to claim 1, wherein $R^2$ is a phenyl-lower alkyl group which may have, on the phenyl ring, 1 to 3 substituents selected from the group consisting of a hydroxyl group, a phenyl-lower alkoxyl group, a lower alkyl group, a lower alkoxy group and a halogen atom.

4. The piperazine compound or salt thereof according to claim 1, wherein $R^2$ is an imidazolyl-substituted lower alkyl group which may have one or more phenyl-lower alkyl groups as substituents on the imidazolyl ring.

5. The piperazine compound or salt thereof according to claim 1, wherein $R^2$ is a group of the formula:

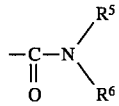

6. The piperazine compound or salt thereof according to claim 3, wherein $R^3$ is a hydrogen atom.

7. The piperazine compound or salt thereof according to claim 3, wherein $R^3$ is a lower alkyl group or a phenyl-lower alkyl group.

8. The piperazine compound or salt thereof according to claim 4, wherein $R^3$ is a hydrogen atom.

9. The piperazine compound or salt thereof according to claim 4, wherein $R^3$ is a lower alkyl group or a phenyl-lower alkyl group.

10. The piperazine compound or salt thereof according to claim 5, wherein $R^3$ is a hydrogen atom.

11. The piperazine compound or salt thereof according to claim 5, wherein $R^3$ is a lower alkyl group or a phenyl-lower alkyl group.

12. The piperazine compound or salt thereof according to any one of claims 6 to 11, wherein $R^4$ is a hydroxyl group.

13. The piperazine compound or salt thereof according to any one of claims 6 to 11, wherein $R^4$ is a phenyl-lower alkoxy group or a tetrahydropyranyloxy group.

14. The piperazine compound or salt thereof according to claim 2, wherein $R^7$ is a lower alkoxycarbonyl group-substituted lower alkyl group.

15. The piperazine compound or salt thereof according to claim 2, wherein $R^7$ and $R^8$ form a trimethylene group by combining together.

16. The piperazine compound or salt thereof according to claim 2, wherein $R^7$ is a lower alkyl group, a phenyl-lower alkyl group which may have, on the phenyl ring, one or more substituents selected from the group consisting of a hydroxyl group and a phenyl-lower alkoxyl group, a lower alkylthio group-substituted lower alkyl group, a phenyl-lower alkoxy group-substituted lower alkyl group, a lower alkoxycarbonyl group, or a hydroxyl group-substituted lower alkyl group.

17. The piperazine compound or salt thereof according to any one of claims 14 to 16, wherein $R^9$ is a hydroxyl group.

18. The piperazine compound or salt thereof according to any one of claims 14 to 16, wherein $R^9$ is a phenyl-lower alkoxy group.

19. (3RS, 6RS)-1-Hydroxy-3-(3,5-di-tert-butyl-4-hydroxybenzyl)-6-isobutylpiperazin-2,5-dione.

20. (3RS, 6SR)-1-Hydroxy-3-(3,5-di-tert-butyl-4-hydroxybenzyl)-6-isobutylpiperazin-2,5-dione.

21. (3RS, 6RS)-1-Hydroxy-6-(3-indolylmethyl)-3-ethoxycarbonylmethylpiperazin-2,5-dione.

22. (3RS, 6SR)-1-Hydroxy-6-(3-indolylmethyl)-3-ethoxycarbonylmethylpiperazin-2,5-dione.

23. (3S, 6R)-1-Hydroxy-6-(3-indolylmethyl)-3-ethoxycarbonylmethylpiperazin-2,5-dione.

24. A pharmaceutical composition for inhibiting superoxide radicals which contains, as the active ingredient, a therapeutically effective amount of a piperazine compound or salt thereof of claim 1 and a pharmaceutically acceptable carrier.

25. A pharmaceutical composition for inhibiting superoxide radicals which contains, as the active ingredient, a therapeutically effective amount of a piperazine compound or salt thereof of claim 2 and a pharmaceutically acceptable carrier.

26. A pharmaceutical composition for preventing and treating diseases or symptoms being caused by superoxide radicals which contains, as the active ingredient, a therapeutically effective amount of a piperazine compound or salt thereof of claim 1 and a pharmaceutically acceptable carrier.

27. A pharmaceutical composition for preventing and treating diseases or symptoms being caused by superoxide radicals which contains, as the active ingredient, a therapeutically effective amount of a piperazine compound or salt thereof of claim 2 and a pharmaceutically acceptable carrier.

28. A pharmaceutical composition for preventing and treating nephritis which contains, as the active ingredient, a therapeutically effective amount of a piperazine compound or salt thereof of claim 1 and a pharmaceutically acceptable carrier.

29. A pharmaceutical composition for preventing and treating nephritis which contains, as the active ingredient, a therapeutically effective amount of a piperazine compound or salt thereof of claim 2 and a pharmaceutically acceptable carrier.

30. Process for preparing a piperazine compound of the formula:

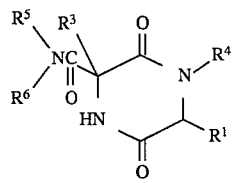

wherein $R^1$ is a lower alkyl group;

$R^3$ is a hydrogen atom, a lower alkyl group or a phenyl-lower alkyl group;

$R^4$ is a hydroxyl group, a phenyl-lower alkoxy group or a tetrahydropyranyloxy group; and $R^5$ and $R^6$ are the same or different, and are each a hydrogen atom, a benzothiazolyl group, or a phenyl-lower alkyl group which may have, on the phenyl ring, 1 to 3 substituents selected from the group consisting of a lower alkoxy group, a phenyl-lower alkoxy group, a lower alkyl group and a hydroxyl group; further, said $R^5$ and $R^6$ and the adjacent nitrogen atom being bonded thereto, together with or without another nitrogen atom or an oxygen atom, may form a 5- to 6-membered saturated heterocyclic group; said heterocyclic group may have, as substituents, one or more phenyl groups which may have one or more lower alkoxy groups as substituents on the phenyl ring;

by reacting a compound of the formula:

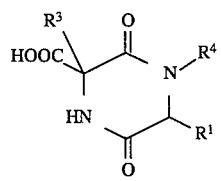 (3)

(wherein $R^1$, $R^3$ and $R^4$ are the same as defined above) with a compound of the formula:

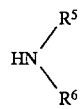 (4)

(wherein $R^5$ and $R^6$ are the same as defined above).

* * * * *